(12) United States Patent
Niemeyer et al.

(10) Patent No.: US 8,093,893 B2
(45) Date of Patent: Jan. 10, 2012

(54) ROCK AND FLUID PROPERTIES PREDICTION FROM DOWNHOLE MEASUREMENTS USING LINEAR AND NONLINEAR REGRESSION

(75) Inventors: Eick Niemeyer, Niedersachsen (DE);
Ansgar Cartellieri, Lower Saxony (DE);
Tobias Kischkat, Niedersachsen (DE);
Mouin Hamdan, Niedersachsen (DE)

(73) Assignee: Baker Hughes Incorporated, Houston, TX (US)

( * ) Notice: Subject to any disclaimer, the term of this patent is extended or adjusted under 35 U.S.C. 154(b) by 251 days.

(21) Appl. No.: 12/327,700

(22) Filed: Dec. 3, 2008

(65) Prior Publication Data
US 2009/0125239 A1    May 14, 2009

Related U.S. Application Data

(63) Continuation-in-part of application No. 11/084,322, filed on Mar. 18, 2005, now Pat. No. 7,495,436.

(51) Int. Cl.
*G01V 3/00*    (2006.01)
(52) U.S. Cl. ........................................ 324/303
(58) Field of Classification Search ........... 324/300–322
See application file for complete search history.

(56) References Cited

U.S. PATENT DOCUMENTS

| | | | |
|---|---|---|---|
| 4,973,111 A | 11/1990 | Haacke et al. | |
| 5,023,551 A | 6/1991 | Kleinberg et al. | |
| 5,363,041 A | 11/1994 | Sezginer | |
| 5,517,115 A | 5/1996 | Prammer | |
| 5,696,448 A | 12/1997 | Coates et al. | |
| 5,936,405 A | 8/1999 | Prammer et al. | |
| 6,040,696 A | 3/2000 | Ramakrishnan et al. | |
| 6,242,912 B1 | 6/2001 | Prammer et al. | |
| 6,247,542 B1 | 6/2001 | Kruspe et al. | |
| 6,400,148 B1 * | 6/2002 | Meyer et al. | 324/303 |
| 6,420,869 B1 * | 7/2002 | DiFoggio | 324/303 |
| 6,512,371 B2 | 1/2003 | Prammer | |
| 6,603,309 B2 * | 8/2003 | Forgang et al. | 324/303 |
| 6,646,437 B1 | 11/2003 | Chitale et al. | |
| 6,755,247 B2 * | 6/2004 | Moake et al. | 166/250.07 |
| 6,816,266 B2 * | 11/2004 | Varshneya et al. | 356/477 |
| 6,838,964 B1 * | 1/2005 | Knight et al. | 335/216 |
| 6,939,515 B2 * | 9/2005 | Carlson et al. | 422/101 |
| 7,034,528 B2 | 4/2006 | Minh et al. | |
| 7,084,392 B2 * | 8/2006 | DiFoggio et al. | 250/269.1 |
| 7,091,719 B2 * | 8/2006 | Freedman | 324/303 |
| 7,187,790 B2 * | 3/2007 | Sabol et al. | 382/128 |
| 7,214,933 B2 * | 5/2007 | DiFoggio et al. | 250/269.1 |
| 7,277,796 B2 * | 10/2007 | Kuchuk et al. | 702/7 |

(Continued)

OTHER PUBLICATIONS

M.N. Miller et al.; "Spin Echo Magnetic Resonance Logging: Porosity and Free Fluid Index Determination," Technical Conference and Exhibition of the Society of Petroleum Engineers, New Orleans, LA, SPE 20561, Sep. 23-26, 1990, pp. 321-334.

*Primary Examiner* — Dixomara Vargas
(74) *Attorney, Agent, or Firm* — Mossman Kumar & Tyler PC

(57) ABSTRACT

Measurements of fluorescence spectra of fluid samples recovered downhole are processed to give the fluid composition. The processing may include a principal component analysis followed by a clustering method or a neutral network. Alternatively the processing may include a partial least squares regression. The latter can give the analysis of a mixture of three or more fluids.

20 Claims, 16 Drawing Sheets

U.S. PATENT DOCUMENTS

| | | | |
|---|---|---|---|
| 7,309,983 B2 * | 12/2007 | Freedman | 324/303 |
| 7,372,264 B2 * | 5/2008 | Akkurt et al. | 324/303 |
| 7,490,085 B2 * | 2/2009 | Walker et al. | 1/1 |
| 7,495,436 B2 * | 2/2009 | Hamdan et al. | 324/303 |
| 7,526,953 B2 * | 5/2009 | Goodwin et al. | 73/152.28 |
| 7,804,296 B2 * | 9/2010 | Flaum et al. | 324/303 |
| 2002/0153887 A1 | 10/2002 | Taicher | |
| 2002/0167314 A1 | 11/2002 | Prammer | |
| 2003/0231017 A1 | 12/2003 | Kiesl et al. | |
| 2004/0041562 A1 | 3/2004 | Speier | |
| 2004/0169511 A1 | 9/2004 | Minh et al. | |
| 2005/0206378 A1 | 9/2005 | Hamdan et al. | |

\* cited by examiner

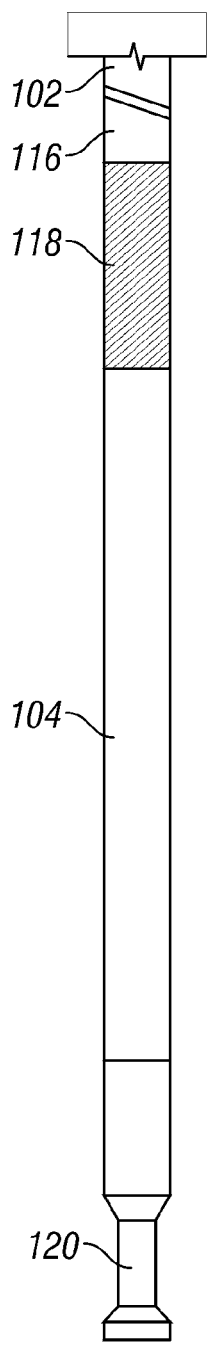
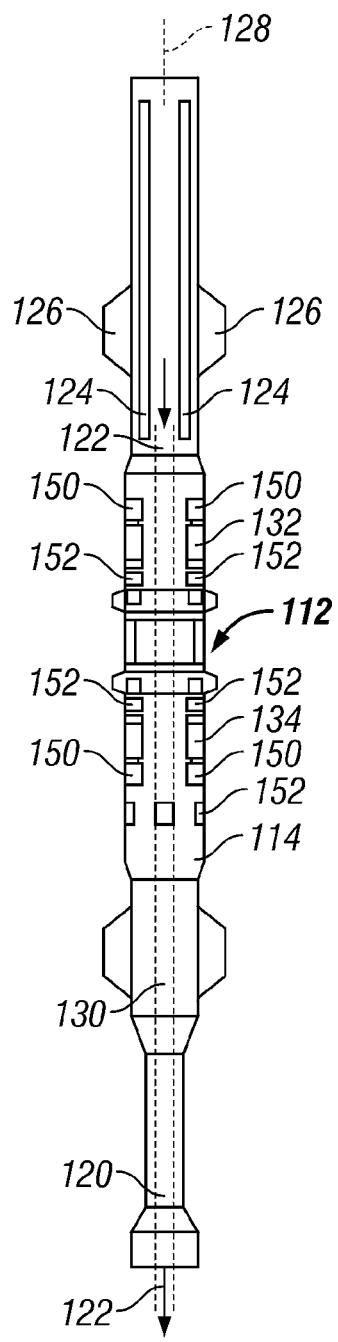
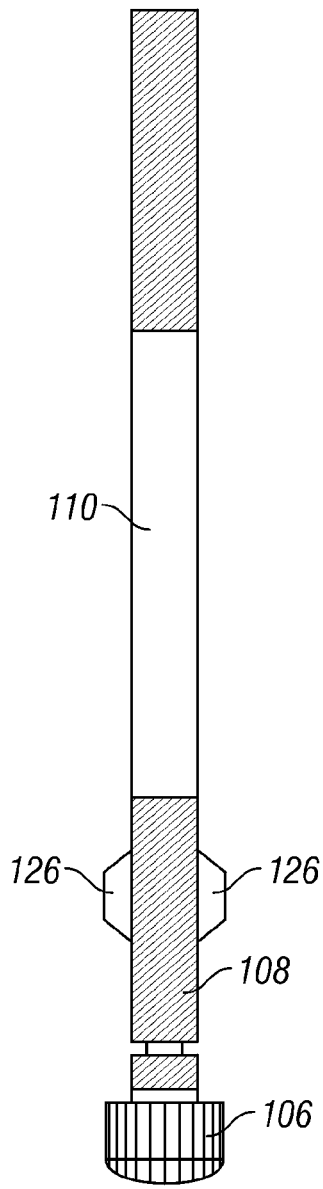
FIG. 2A
(Prior Art)
FIG. 2B
(Prior Art)
FIG. 2C
(Prior Art)

ROCK AND FLUID PROPERTIES PREDICTION FROM DOWNHOLE MEASUREMENTS USING LINEAR AND NONLINEAR REGRESSION

CROSS-REFERENCES TO RELATED APPLICATIONS

This application claims priority as a Continuation-in-part of U.S. patent application Ser. No. 11/084,322 filed on Mar. 18, 2005 with a priority claim to U.S. Provisional Patent Application Ser. No. 60/554,121 filed on Mar. 18, 2004.

BACKGROUND OF THE DISCLOSURE

1. Field of the Disclosure

The disclosure is related to the field of Nuclear Magnetic Resonance (NMR) apparatus and methods. In particular, the disclosure is directed towards the use of regression techniques for analysis of NMR data and for determination of the properties of materials being examined using a NMR apparatus.

2. Description of the Related Art

The description of the disclosure and its background are approached in the context of measurement while drilling apparatus and methods for analysis of properties of earth formation. It is to be understood that the disclosure is not limited to this field of study.

NMR methods are among the most useful non-destructive techniques of material analysis. When hydrogen nuclei are placed in an applied static magnetic field, a small majority of spins are aligned with the applied field in the lower energy state, since the lower energy state in more stable than the higher energy state. The individual spins precess about the applied static magnetic field at a resonance frequency also termed as Larmor frequency. This frequency is characteristic to a particular nucleus and proportional to the applied static magnetic field. An alternating magnetic field at the resonance frequency in the Radio Frequency (RF) range, applied by a transmitting antenna to a subject or specimen in the static magnetic field flips nuclear spins from the lower energy state to the higher energy state. When the alternating field is turned off, the nuclei return to the equilibrium state with emission of energy at the same frequency as that of the stimulating alternating magnetic field. This RF energy generates an oscillating voltage in a receiver antenna whose amplitude and rate of decay depend on the physicochemical properties of the material being examined. The applied RF field is designed to perturb the thermal equilibrium of the magnetized nuclear spins, and the time dependence of the emitted energy is determine by the manner in which this system of spins return to equilibrium magnetization. The return is characterized by two parameters: $T_1$, the longitudinal or spin-lattice relaxation time; and $T_2$, the transverse or spin-spin relaxation time.

Measurements of NMR parameters of fluid filling the pore spaces of the earth formations such as relaxation times of the hydrogen spins, diffusion coefficient and/or the hydrogen density is the bases for NMR well logging. NMR well logging instruments can be used for determining properties of earth formations including the fractional volume of pore space and the fractional volume of mobile fluid filling the pore spaces of the earth formations.

Various sequences (selectable length and duration) of RF magnetic fields are imparted to the material, which are being investigated to momentarily re-orient the nuclear magnetic spins of the hydrogen nuclei. RF signals are generated by the hydrogen nuclei as they spin about their axes due to precession of the spin axes. The amplitude, duration and spatial distribution of these RF signals are related to properties of the material which are being investigated by the particular NMR techniques being used. In the well logging environment, contrast is high between free and bound fluids based on their relaxation times, between oil and water based on their relaxation times and diffusion coefficient. Based on NMR measurements, it is possible to infer something about the porosity distribution of earth formations and the fluids therein.

Methods of using NMR measurements for determining the fractional volume of pore space and the fractional volume of mobile fluid are described, for example, in *Spin Echo Magnetic Resonance Logging: Porosity and Free Fluid Index Determination*, M. N. Miller et al, Society of Petroleum Engineers paper no. 20561, Richardson, Tex., 1990. In porous media there is a significant difference in T1 and T2 relaxation time spectrum of fluids mixture filling the pore space. Thus, for example, light hydrocarbons and gas may have T1 relaxation time of about several seconds, while T2 may be thousand times less. This phenomenon is due to diffusion effect in internal and external static magnetic field gradients. Internal magnetic field gradients are due to magnetic susceptibility difference between rock formation matrix and pore filling fluid.

Since oil is found in porous rock formation, the relationships between porous rocks and the fluids filling their pore spaces are extremely complicated and difficult to model. Nuclear magnetic resonance is sensitive to main petrophysical parameters, but has no capabilities to establish these complex relationships. Oil and water are generally found together in reservoir rocks. Since most reservoir rocks are hydrophilic, droplets of oil sit in the center of pores and are unaffected by the pore surface. The water-oil interface normally does not affect relaxation, therefore, the relaxation rate of oil is primarily proportional to its viscosity. However, such oil by itself is a very complex mixture of hydrocarbons that may be viewed as a broad spectrum of relaxation times. In a simplest case of pure fluid in a single pore there are two diffusion regimes that govern the relaxation rate. Rocks normally have a very broad distribution of pore sizes and fluid properties. Thus it is not surprising that magnetization decays of fluid in rock formations are non-exponential. The most commonly used method of analyzing relaxation data is to calculate a spectrum of relaxation times. The Carr-Purcell-Meiboom-Gill (CPMG) pulse sequence is used to determine the transverse magnetization decay. The non-exponential magnetization decays are fit to the multi-exponential form:

$$M(t) = \sum_{i=1}^{L} m(T_{2i}) e^{-t/T_{2i}} \quad (1)$$

where M(t) represents the spin echo amplitudes, equally spaced in time, and the $T_{2i}$ are predetermined time constants, equally spaced on a logarithm scale, typically between 0.25 ms and 4000 ms. The set of m are found using a regularized nonlinear least squares technique. The function $m(T_{2i})$, conventionally called a $T_2$ distribution, usually maps linearly to a volumetrically weighted distribution of pore sizes.

The calibration of this mapping is addressed in several publications. Prior art solutions seek a solution to the problem of mathematical modeling of the received echo signals by the use of several techniques, including the use of non-linear regression analysis of the measurement signal; non-linear least square fit routines, as disclosed in U.S. Pat. No. 5,023, 551 to Kleinberg et al, and others. Other prior art techniques include a variety of signal modeling techniques, such as polynomial rooting, singular value decomposition (SVD) and miscellaneous refinements thereof, to obtain a better approximation of the received signal. A problem with prior art signal compressions is that some information is lost.

U.S. Pat. No. 4,973,111 to Haacke describes a method for parametric image reconstruction from sampled NMR measurement data. In the method disclosed therein, the desired object function is approximated by a series of known model functions having a finite number of unknown parameters. Because the direct equations are highly non-linear, the problem is simplified by using all-pole parameter estimation, in which the unknown parameters are the roots of a polynomial equation. The coefficients of this equation are obtained as the solution vector to a system of linear prediction equations, which involve the received measurement data. The solution of the linear prediction system, as suggested in Haacke, is found by applying Singular Value Decomposition (SVD) to the linear prediction data matrix of the measurement signal. This approach is shown to reduce the effects of the measurement noise and estimate the order of the model functions.

Due to the large size of the involved matrices, however, the method of Haacke is computationally quite intensive and while suitable for off-line processing does not lend itself to real-time applications of NMR well logging. In addition, the method does not take into account information about the material under investigation or the measurement process, which can be used to simplify the computations.

U.S. Pat. No. 5,363,041 to Sezginer teaches use of a SVD and compression of raw NMR data and further a non-negative linear least square fit to obtain a distribution function. U.S. Pat. No. 5,517,115 to Prammer discloses a method of using a priori information about the nature of the expected signals to obtain an approximation of the signal using a set of preselected basis functions. A singular value decomposition is applied to a matrix incorporating information about the basis functions, and is stored off-line in a memory. During the actual measurement, the apparatus estimates a parameter related to the SNR of the received NMR echo trains and uses it to determine a signal approximation model in conjunction with the SVD of the basis function matrix.

All of the above discussed prior art methods rely on a two step procedure. For example, in the first step, the NMR data are inverted to give a distribution of relaxation times ($T_1$ or $T_2$). In the second step, some inference is drawn about the formation fluids and porosity distribution based on the relaxation time distribution. There is a certain amount of empiricism involved in each of the steps of the two step procedure, resulting in possible accumulation of errors from the individual steps. The two step procedure is avoided in U.S. Pat. No. 6,040,696 to Ramakrishnan et al. wherein an inversion method is used to derive parameters of the pore distribution in carbonates.

Thus, notwithstanding the advances in the prior art, it is perceived that the problems involved in the parameter model estimation used in NMR sensing methods for well logging have not yet been resolved. No efficient solutions have been proposed to combine advanced mathematical models with simple signal processing algorithms to increase the accuracy and numerical stability of the parameter estimates. Existing solutions require the use of significant computational power which makes the practical use of those methods inefficient, and frequently impossible to implement in real-time applications.

SUMMARY OF THE DISCLOSURE

One embodiment of the disclosure is a method of estimating a value of a property of a fluid recovered from an earth formation. The method includes conveying a sensing apparatus into a borehole in the earth formation, using the sensing apparatus for making a plurality of measurements indicative of the property of the fluid recovered from the earth formation, using a predictive model to estimate from the measured plurality of measurements the value of the property, and recording the estimated value of the property on a computer readable medium, wherein the predictive model is obtained by a regression in which the dependent variable of the regression comprises a matrix of values of the measurements indicative of the property obtained from a plurality of fluid samples having a known value of the property, and in which the independent variable of the regression comprises the known value of the property.

Another embodiment of the disclosure is an apparatus configured to estimate a value of a property of a fluid recovered from an earth formation. The apparatus includes a sensing apparatus configured to be conveyed into a borehole and make a plurality of measurements indicative of the property of the fluid recovered from the earth formation, and a processor configured to (i) use a predictive model to estimate from the measured plurality of measurements the value of the property; and (ii) record the estimated value of the property on a computer readable medium, wherein the predictive model is obtained by a regression in which the dependent variable of the regression comprises a matrix of values of the measurements indicative of the property obtained from a plurality of fluid samples having a known value of the property, and in which the independent variable of the regression comprises the known value of the property.

Another embodiment of the disclosure is a computer-readable medium accessible to at least one processor. The computer-readable medium including instructions which enable the at least one processor to estimate a value of a property of a fluid recovered from an earth formation using measurements made by a sensing apparatus on the fluid and a predictive model obtained by a regression in which the dependent variable of the regression comprises a matrix of values of the measurements indicative of the property obtained from a plurality of fluid samples having a known value of the property, and in which the independent variable of the regression comprises the known value of the property, and record the estimated value of the property on a computer readable medium.

Another embodiment of the disclosure is a method of estimating a value of a property of a fluid recovered from an earth formation. The method includes conveying a sensing apparatus into a borehole in the earth formation, using the sensing apparatus for making a plurality of measurements indicative of the property of the fluid recovered from the earth formation, using a predictive model to estimate from the plurality of measurements the value of the property, and recording the estimated value of the property on a computer readable medium, wherein the predictive model is obtained by analysis of a projection of the measurements on a plurality of principal components of measurements indicative of the property obtained from a plurality of fluid samples having a known value of the property.

Another embodiment of the disclosure is an apparatus configured to estimate a value of a property of a fluid recovered from an earth formation. The apparatus includes a sensing apparatus configured to be conveyed into a borehole and make a plurality of measurements indicative of the property of the fluid recovered from the earth formation; and a processor configured to (i) use a predictive model to estimate from the measured plurality of measurements the value of the property, and (ii) record the estimated value of the property on a computer readable medium, wherein the predictive model is obtained by analysis of a projection of the measurements on a plurality of principal components of measurements indicative of the property obtained from a plurality of fluid samples having a known value of the property.

Another embodiment of the disclosure is a computer-readable medium accessible to at least one processor. The computer-readable medium including instructions which enable the at least one processor to estimate a value of a property of a fluid recovered from an earth formation using measurements made by a sensing apparatus on the fluid and a predictive model obtained by analysis of a projection of the measurements on a plurality of principal components of measurements indicative of the property obtained from a plurality of fluid samples having a known value of the property; and record the estimated value of the property on a computer readable medium.

BRIEF DESCRIPTION OF THE DRAWINGS

The present disclosure is best understood with reference to the accompanying drawings in which like numerals refer to like elements, and in which:

FIGS. 2A-2C (Prior Art) illustrate additional details about an exemplary NMR sensor assembly;

DESCRIPTION OF AN EMBODIMENT

An NMR well logging apparatus which is suitable for use with this disclosure is described, for example, in U.S. Pat. No. 6,247,542 to Kruspe et al., the contents of which are fully incorporated herein by reference. The device in Kruspe is for exemplary purposes only and the method of the present disclosure may be used with any NMR well logging apparatus including one conveyed on a wireline. As taught by Kruspe, the NMR sensor assembly is slidably coupled to the longitudinal member wherein the sensor assembly includes at least one sensor for obtaining measurements relating to the parameter of interest. When the sensor assembly is held in a non-rotating position, for instance, for obtaining the measurements, the longitudinal member is free to rotate and continue drilling the borehole. The sensor assembly is slidably coupled to the longitudinal member using, for example, at least one guide sleeve slidably coupled to the longitudinal member. The sensor assembly further includes, for example, at least one transmitter. The sensor assembly of the present disclosure can include any of a variety of sensors and/or transmitters for determining a plurality of parameters of interest including, for example, nuclear magnetic resonance measurements. The device of Kruspe makes it possible, for example, to obtain NMR measurements with the NMR assembly clamped to the borehole while drilling continues. It should further be noted that the method of the present disclosure is not limited in its applicability to in situ determination of properties of earth formations and can equally well be applied to determination of properties of rock samples, cores and fluid samples recovered from earth formations as well as to laboratory measurements.

Figure 1:
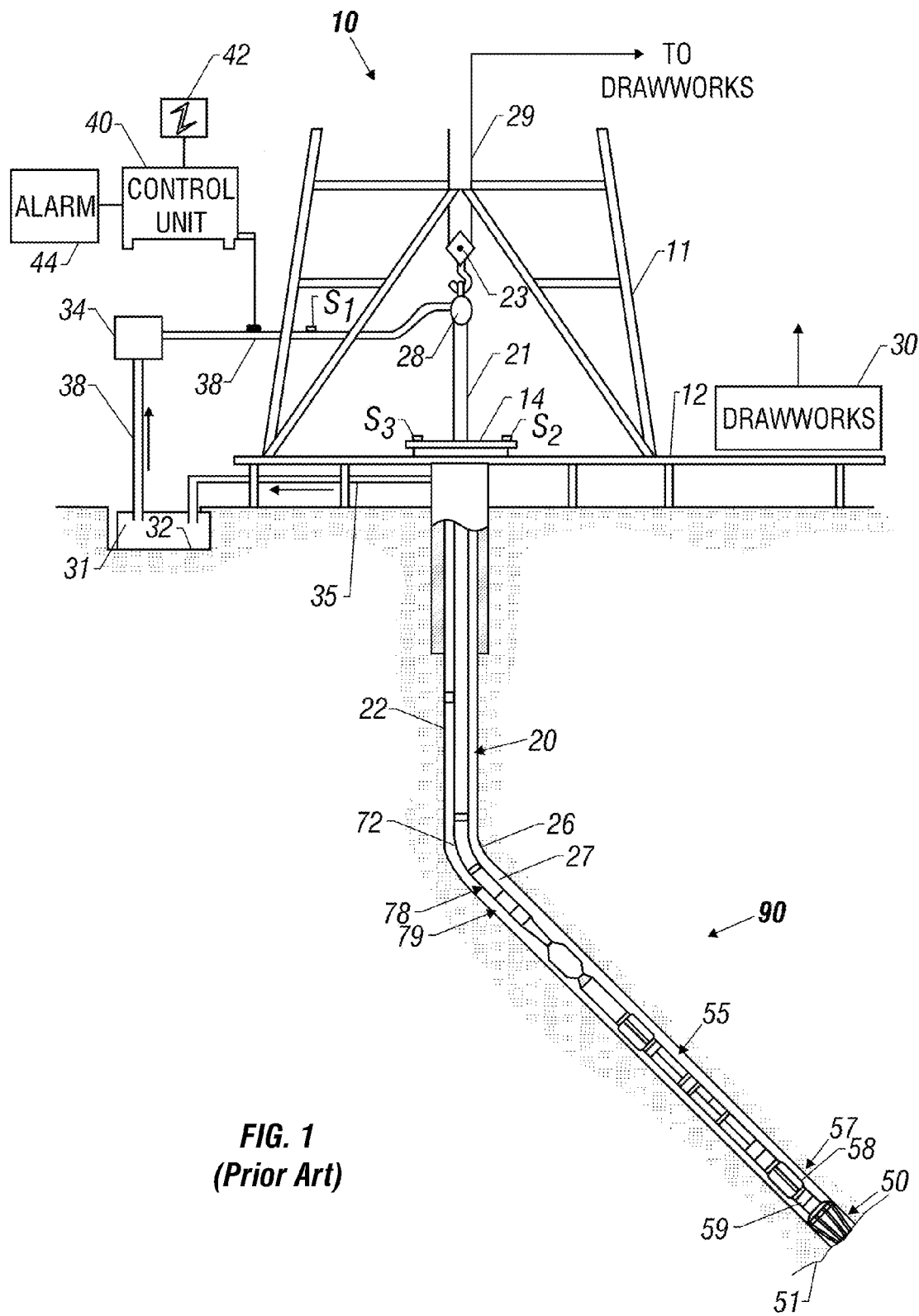
FIG. 1 (Prior Art) shows a measurement-while-drilling device suitable for use with the current disclosure.

FIG. 1 (Prior Art) shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ may be placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In the embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters may include include bit bounce, stick-slip of the drilling assembly, backward rotation, torque, shocks, borehole and annulus pressure, acceleration measurements and other measurements of the drill bit condition. A suitable telemetry or communications sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 may include a computer or a microprocessor-based processing system, memory for storing programs or models and data, a recorder for recording data, and other peripherals. The control unit 40 may be adapted to activate alarms 44 when certain unsafe or undesirable operating conditions occur.

Referring to FIGS. 2A-2C, additional details of an exemplary NMR sensor assembly are discussed. An exemplary drilling assembly 100 at the end of a drill string 102 or coiled tubing is illustrated. A measurement-while-drilling (MWD) tool 104, an associated pulsed nuclear magnetic resonance (NMR) tool 112 (contained within a housing 114) and electronic circuitry 124, and a pulsed power unit 118 are connected in tandem in the drilling assembly 100. Flex subs 120 are used for example in connecting the MWD tool 104 and the NMR tool 112 in the drilling assembly 100. The MWD tool 104 may also include a sonic sensor, a density measurement tool, and a porosity measurement tool. A communication sub 116 using, for example, two-way telemetry, is also provided as illustrated in the drilling assembly 100. The drilling assembly is also provided with a plurality of motion sensors 152 for sensing the motion of the tool within the borehole. In one embodiment of the disclosure, the motion sensors are accelerometers that sense the three components of acceleration of the tool.

The drilling assembly 100 includes a drill bit 106, bearing assembly 108, and downhole mud motor 110. The drill string 102 includes, for example, sections of drill pipe connected end-to-end or a generally continuous coiled. The borehole typically contains a drilling fluid 122 or "mud" which is forced through the drill string 102 and the bottom hole drilling assembly 100 through the drill bit 106. A channel 130 within the drill string 102 and drilling assembly 100 allows the drilling fluid 122 through the drill string 102 and drilling assembly 100. The drilling fluid acts to lubricate the drill bit 106 and to carry borehole cutting or chips away from the drill bit 106.

The communication sub 116, power unit 118, MWD tool 104, and NMR tool 112 are all connected in tandem with the drill string 102. Such subs and tools form a bottom hole drilling assembly 100 between the drill string 102 and the drill bit 106. Stabilizers 126 are used to stabilize and center the drilling assembly 100 and tools within the borehole. The housing 114, for example, a drilling collar, is made of a nonmagnetic alloy. The drilling assembly 100 makes various measurements including pulsed nuclear magnetic resonance measurements while the borehole is being drilled. As seen in FIG. 2B, the NMR tool is rotationally symmetric about a longitudinal axis 128 of the drilling assembly 100.

In one embodiment, pulsed NMR tool 112 includes at least two spaced-apart magnets 132 and 134 housed in the drilling assembly 100 and within the NMR tool 112 for producing a static magnetic field having a region of substantially uniform magnetic intensity in the vicinity of the borehole. The at least two spaced-apart magnets 132 and 134 are tubular in shape and arranged coaxially within the NMR tool 112 and to surround the channel 130. A radio frequency (RF) transmitting antenna or coil 136 also surrounds the channel 130 and is located, for example, between the two spaced-apart magnets 132 and 134. The RF coil 136 is connected to a suitable RF pulse transmitter such as the pulsed power unit 118 for providing power at selected frequencies and a processor 124 which drives the RF transmitting antenna or RF coil 136. The RF coil 136 is pulsed and creates a high frequency RF field orthogonal to the static magnetic field. The processor also receives the signals from the sensors indicative of the motion of the tool. The processor controls the timing of the pulse sequence on the basis of the signals from the motion sensors. The at least two magnets 132 and 134 are permanently magnetized, for example, in the axial direction and, in one embodiment, are positioned in opposing directions.

Figure 3:
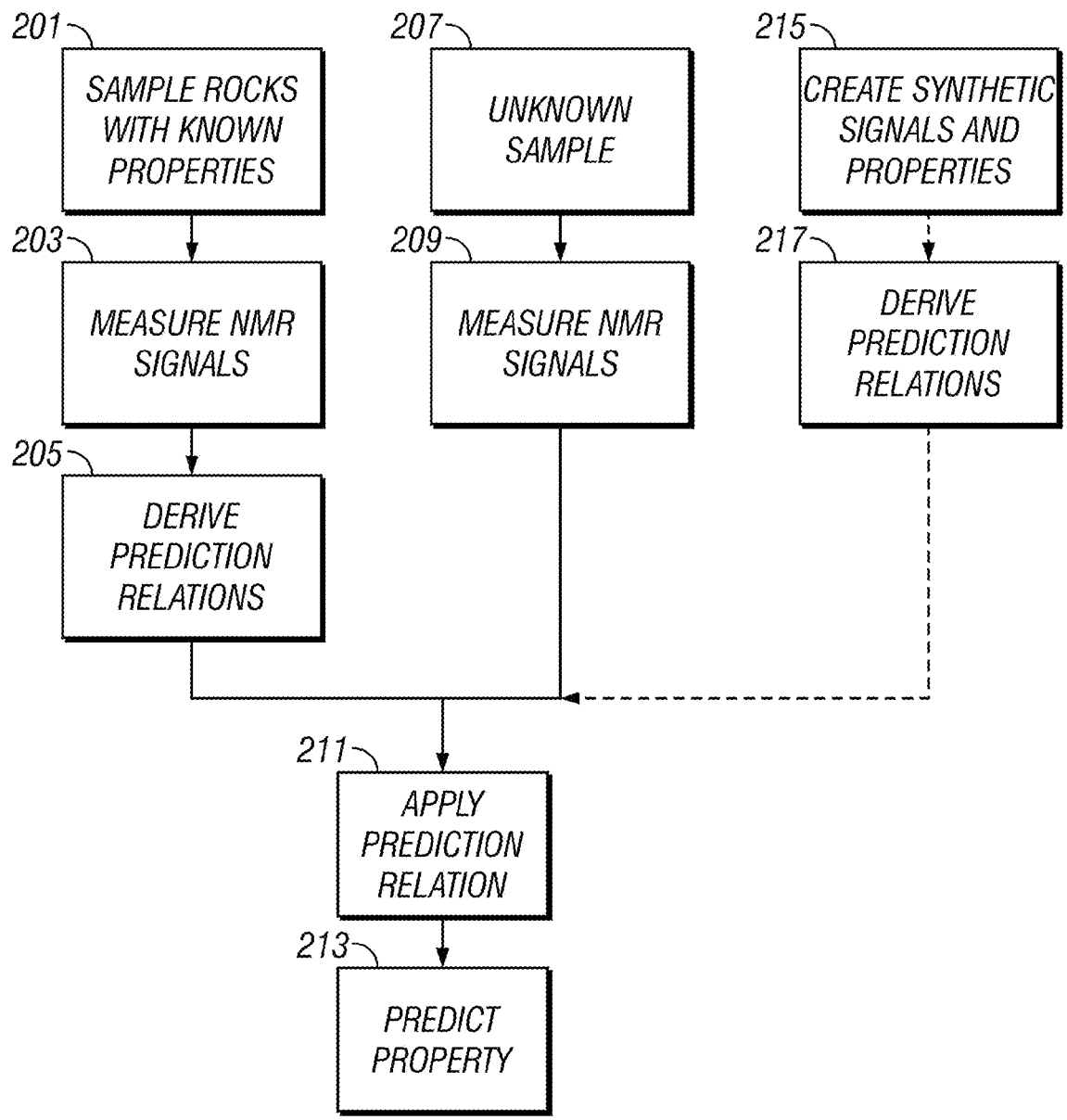
FIG. 3 is a flow chart illustrating steps of the present disclosure.

Referring now to FIG. 3, a flow chart of the method of the present disclosure is shown. Using the NMR device, measurements are obtained 201 on samples having a known property. These measurements are indicative of nuclear spin characteristics of the earth formation within a region of examination. The method of the present disclosure is described in the context of spin echo measurements, but is also applicable to other NMR measurements. These spin echo measurements are obtained using a CPMG sequence or a modified CPMG sequence 203. A common implementation of a modified CPMG sequence may be denoted as $$RFA_{\pm x}\text{-}\tau\text{-}n\cdot(RFB_y\text{-}\tau\text{-}echo\text{-}\tau)\text{-}TW \quad (2)$$

where $RFA_{\pm x}$ is an A pulse, usually 900 tipping pulse and RFB is a refocusing B pulse. In a conventional CPMG sequence, the B pulse has a 180° tipping angle whereas in a modified CPMG sequence the B pulse has a tipping angle less than 180°. The ± phase of RFA is applied alternately in order to identify and eliminate systematic noises, such as ringing and DC offset through subsequent processing. By subtracting the echoes in the − sequence from the pulses in the adjoining + sequence, the ringing due to the B is suppressed.

The measurements are made on a number of samples having known properties. Based on the samples with known properties, a prediction relation is derived 205 relating the measurements to the known properties. For the specific problem of NMR measurements of earth formations, the known samples may be core samples whose properties are well characterized by laboratory measurements. These may be referred to as the training set, and the process of deriving the prediction relation may be called the process of training.

For determination of the properties of an unknown sample 207, the same measurements as were made on the training samples are made 209 on the unknown sample. The prediction relation derived in 205 is then applied 211 to the measurements of the unknown sample to give a predicted value of the property of the unknown sample. In the context of the present disclosure, this process of applying the prediction relation is first tested on a set of samples, called the test set, for which the property is actually known. However, the samples in the test set are not used in the derivation of the prediction relation. Hence if the prediction made on the test set is in agreement with the known properties of the test set, then there is some assurance that the prediction method has some validity. Once such a confirmation of validity is made, the derived prediction method 205 can be applied to truly unknown samples, e.g., in an earth formation. The process of validation is depicted schematically in FIG. 4.

In an alternate embodiment of the disclosure, a different method is used for deriving the prediction relations. Rocks are defined with a known pore size distribution, and using known prior art methods, a $T_2$ distribution is obtained. As an example, two or three peaks of the $T_2$ distribution are specified with different amplitude, location and width. Synthetic NMR signals and properties of interest are then generated (215 in FIG. 3) and a prediction relation is derived 217 as discussed above. Building of a synthetic data set is not limited to this procedure, but can be modified upon any a priori knowledge of the subject of investigation.

Regardless of which of the two methods discussed with reference to FIG. 3 is used for deriving the prediction relations, total porosity PHI as well as partial porosities such as clay-bound water CBW, bound water BW, effective porosity PHE, etc. can be determined by using the well-established cutoff model which assigns part of the $T_2$ distribution to the different partial porosities. There is basically no limitation to replace the estimation of any NMR-related property by a prediction model. This includes properties such as permeability and capillary pressure curves which can be directly connected to an NMR signal by a prediction model. It also includes properties (e.g., water and hydrocarbon saturation) that are commonly estimated by combining NMR data with other measurements such as Resistivity, Density, Neutron, etc. People versed in the art of evaluating NMR data alone or in combination with other measurements can easily see the potential field of applications for the prediction method.

Figure 4:
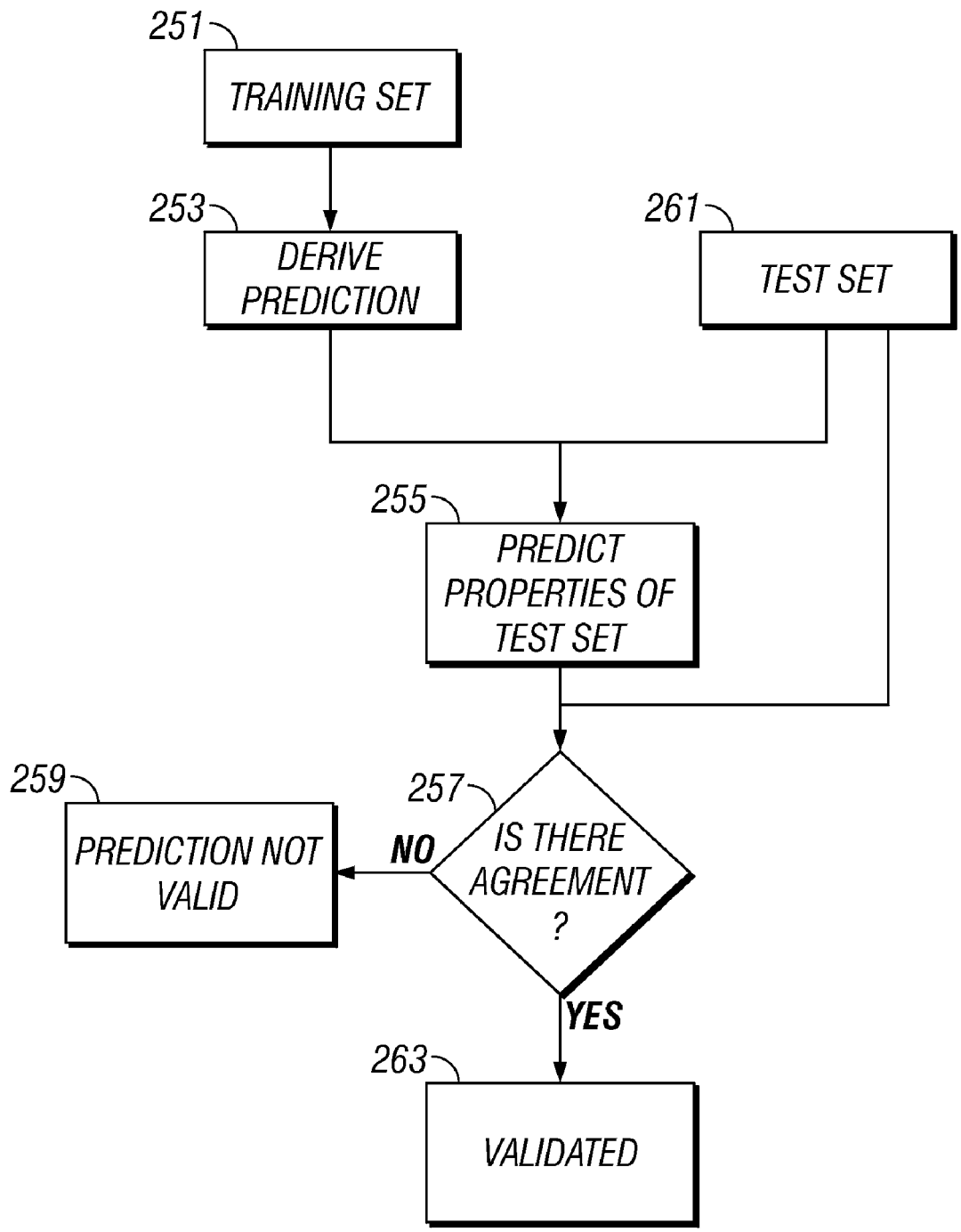
FIG. 4 is a flow chart illustrating the use of training and validation sets of samples.

Shown in FIG. 4 is a training set 251 on which a prediction model is derived 253. Results of the prediction model are applied 255 to measurements from a test set 261. The predicted properties of the test set are compared for agreement 257 with the actual properties of the test set. If there is agreement, the prediction model is validated 263 and may be applied to truly unknown data. If there is no agreement at 257, then it is an indication that the prediction model is invalid 259 and further training is needed. In such a case, the parameters of the training set may be changed.

Figure 5:
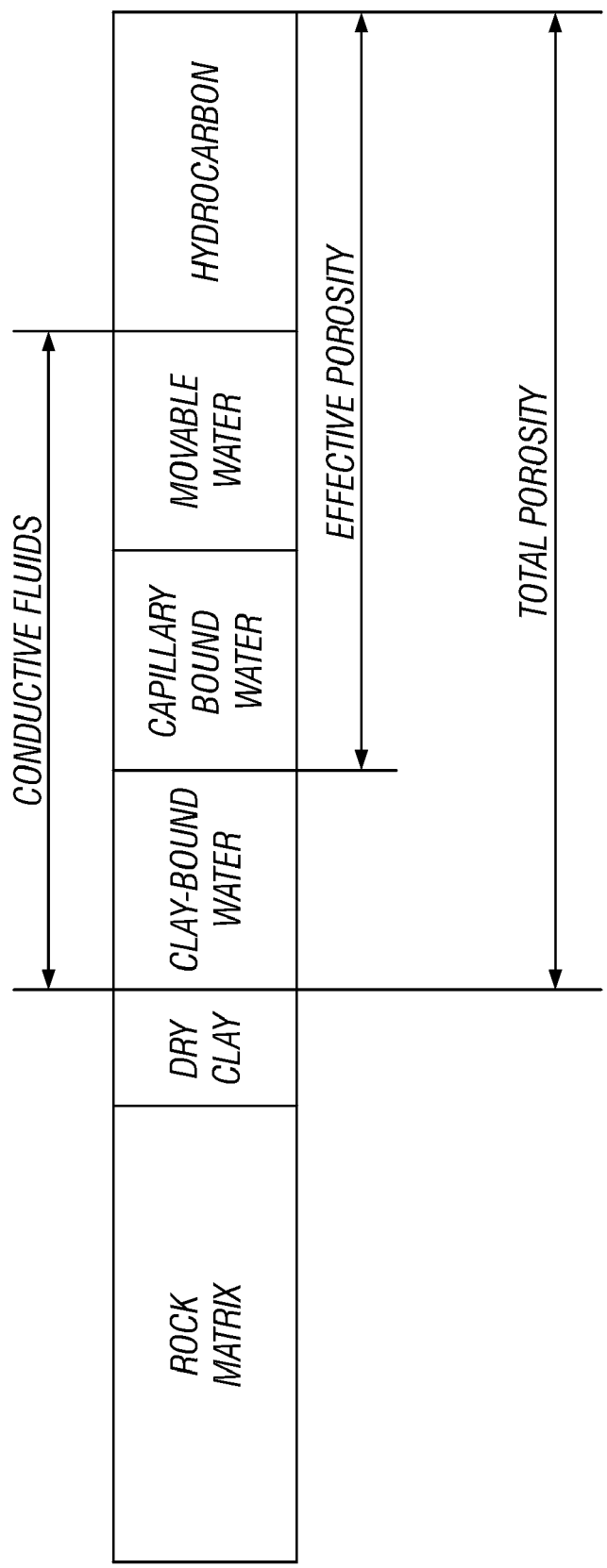
FIG. 5 (Prior Art) illustrates the various components of a fluid in a rock matrix.

As an illustration of the method of the present disclosure, the method of the present disclosure is illustrated using eleven samples from the Shell Rock Catalog of Shell E&P Technology Inc. The choice of the Shell Rock Catalog is a matter of convenience. This is one of many rock catalogs that are commercially available, several of which are provided by Core Laboratories Inc. Eleven sandstone samples from the Shell Rock Catalog were selected. The specific property to which the method of the present disclosure is applied is that of Bound Water. Referring to FIG. 5, this is the sum of clay bound water and capillary bound water and is, at a minimum, an indication of the amount of fluid in a reservoir rock that cannot be recovered. The samples from the Shell Rock Catalog yielded the values of BW given in Table I:

TABLE I

BW Values for selected training samples from Shell Rock Catalog

| # | 1 | 2 | 3 | 4 | 5 | 6 | 7 | 8 | 9 | 10 | 11 |
|---|---|---|---|---|---|---|---|---|---|----|----|
| BW (%) | 12.2 | 6.4 | 7.2 | 11.3 | 3.6 | 12.0 | 14.6 | 3.7 | 8.5 | 11.4 | 15.6 |

Figure 6:
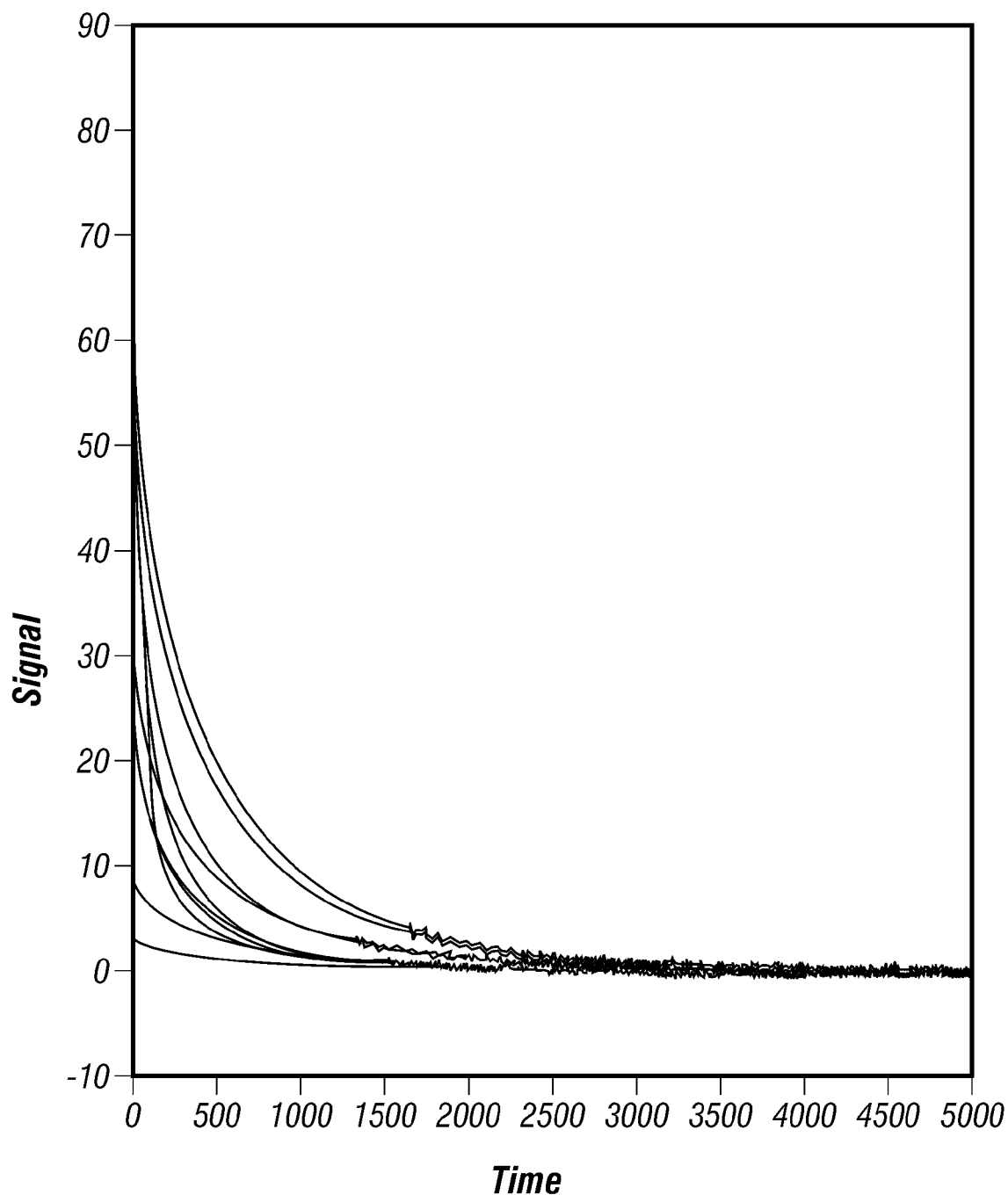
FIG. 6 shows spin echo signals from the training set of Table I used in the present disclosure.

FIG. 6 shows the NMR spin echo signals obtained on the eleven samples. The abscissa is time in milliseconds the ordinate is the spin echo signal In one embodiment of the disclosure, a very simple prediction model was used. The specific method relied on a standard multiple regression analysis in which the independent variable was the BW (see Table I) and the dependent variables were simply the spin echo signals. A standard, off the shelf, Partial Least Squares (PLS) program of Eigenvector Research Incorporated available in conjunction with the MATLAB package was used for the PLS.

We digress briefly to summarize the different types of statistical analysis methods that could be used. The first of these is the classical least squares algorithm. The classical least square (CLS) model assumes that the echo train is a weighted sum of pure linearly independent signals (in this case exponential decays with different time constants $T_{2i}$ similar to equation (1)).

The model equation is:

$$y = w \cdot P$$

where y is the measured echo train(vector), w is a vector weights and P is a matrix of the pure exponentials. Generally, given the measured echo train y, one would like to know w weight vector to which each component of P contributes into the construction of y.

This can be evaluated from:

$$w = y \cdot P^+$$

where $P^+$ is called the generalized inverse of matrix P and defined as:

$$P^+ = P^T(PP^T)^{-1}$$

A drawback of the CLS is that P should contain a complete set of all possible exponential decay that spawns the echo train space and furthermore, some of the weights w could go negative which in our case has no physical meaning.

Given rock property matrix M and their corresponding echo trains matrix X we can estimate the pure components $P_{est}$ that are extracted from X:

$$P_{est}=(M^TM)^{-1}M^TX$$

The regression matrix will be $B=(P_{est}P_{est})^{-1}P_{est}$, and the prediction can be performed as:

$$M_{pred}=B\cdot y$$

The Inverse Least Squares (ILS) regression assumes that a regression vector b can be used to extract the property y of the measured echo train x thus.

$$x \cdot b = y.$$

The regression vector b must be determined from a collection of measured echo trains X with their corresponding properties y. thus:

$$b=X^+y$$

where $X^+$ is called the partial inverse of matrix X.
There are many ways to determine $X^+$ the most common one is the least square.

$$X^+=(X^TX)^{-1}X^T$$

Unfortunately, this approach has always a drawback, colinearity of X. which for small perturbations, systems produce a linear combinations of X variables. In these cases $(X^TX)^{-1}$ would not exist as the matrix X is ill-conditioned.

Principal component regression (PCR) is one way to deal with ill-conditioned matrices (that ILS suffers from). Principal Component Analysis (PCA) is a decomposition method that finds a combination of factors, or components, that describes major trends in a matrix X. This is done by eigenvector decomposition of the covariance matrix of X.

$$cov(X)=(X^TX)/m-1$$

where m is the number of samples in the matrix(rows).

Assuming that the matrix X is autoscaled (mean centered (mean=0 by subtracting the mean of each column) and variance scaled (variance=1 by dividing each column by its standard deviation)).

$$X=TP+E$$

T scores: contains information about how measurements relate to each other.
P Loadings: contains information about how variables relate to each other.
E is the residual.

T forms an orthogonal set ($t_i^T t_j=0$ for $i \neq j$) and P forms an orthonoral set ($p_i^T p_j=0$ for $i \neq j$ and =1 for i=j). The scores $t_i$ of T is a linear combination of X defined by $p_i$ that is to say that $t_i$ is the projection of X on $p_i$.

$$Xp_i=t_i$$

Thus the $X^+$ in the PCR regression is estimated as:

$$X^+=P(T^TT)^{-1}T^T \text{ and}$$

$$b=X^+y \text{ (}b\text{ is the regression vector we are looking for)}$$

It is to be noted that the PCA and subsequently the PCR relies heavily on the number of major components that need to be taken into account. The PCA decomposition is a known method to reduce signal space and in some case reduce noise in the matrix X by taken only few components in reconstructing the matrix X. When taking all decomposition components while regressing, the PCR converges to the ILS solution.

Partial Least Squares (PLS) is a regression that decompose the matrix X while taking into account the relationship that exists between the scores of the X matrix and the scores of the Y matrix. It deals with ill-conditioned matrices (that ILS suffers from) similar to PCR and provide a biased regression vector towards the Y matrix. PCR and PLS regression differ in the methods used in extracting factor scores. In short, PCR produces the weight matrix W reflecting the covariance structure between the X matrix variables, while PLS produces the weight matrix W reflecting the covariance structure between the X matrix and the Y matrix variables.

The modeling equations for PLS are:

$$X=TP^T+E \text{ (similar to PCR)}$$

$$Y=UC^T+F$$

$$U=bT \text{ (}b\text{ is the regression vector that encapsulates the inner relation between X and Y scores.)}$$

Figure 7:
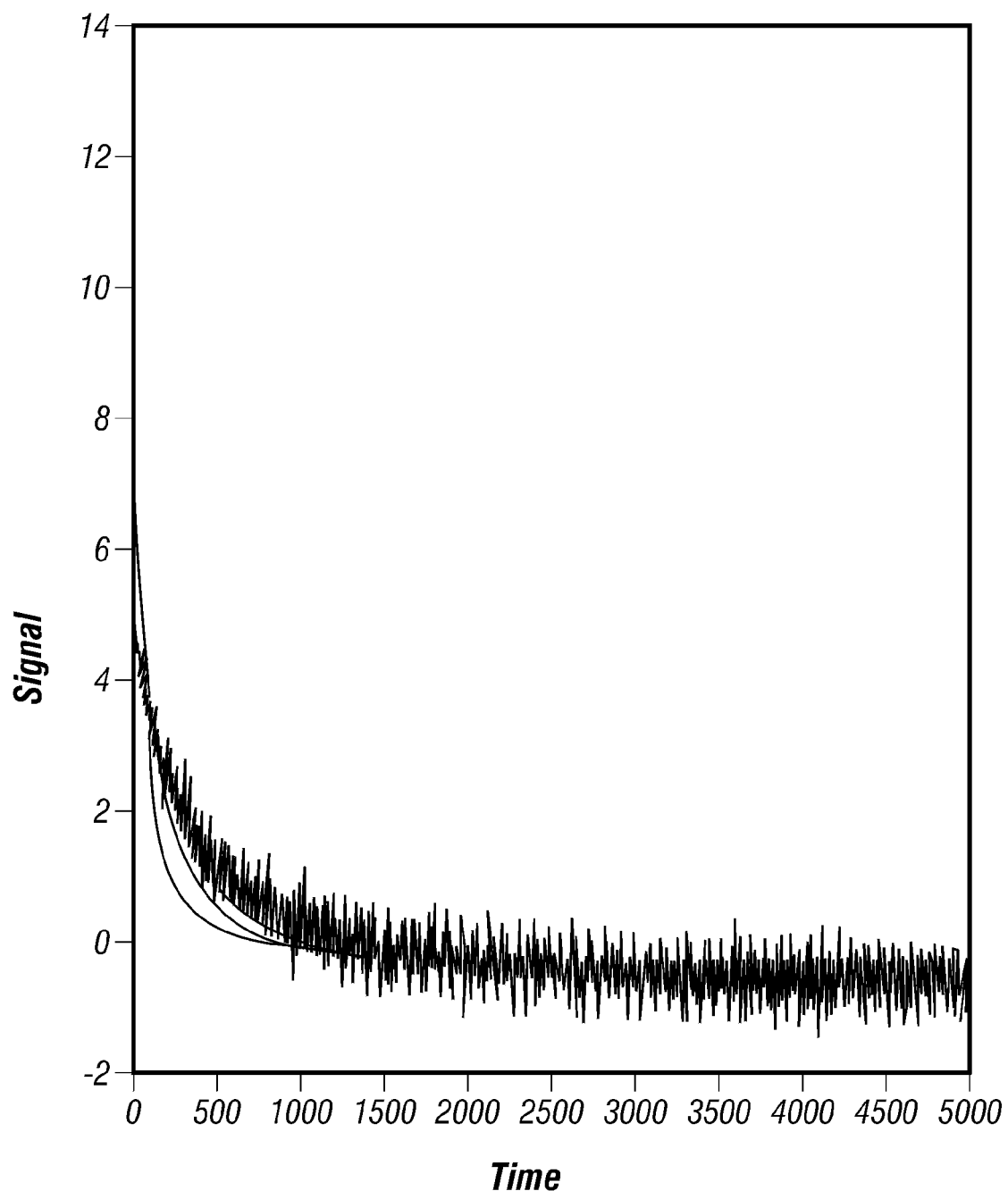
FIG. 7 shows autoscaled spin echo signals from the training set used in the present disclosure.

Referring now to FIG. 6, conventional pre-processing of the data in FIG. 6 may be done by autoscaling. Shown in FIG. 6 are spin echo signals for the eleven samples of Table 1. The preprocessing includes subtracting the mean value of each of the signals to reduce it to zero mean, and normalization to make the variance of each of the signals the same (such as unity, for convenience). The result is given in FIG. 7. The independent variables are also pre-processed in the same way to give the values in Table II:

TABLE II

Autoscaled BW Values for selected training samples from Shell Rock Catalog

| | # | | | | | | | | | | |
|---|---|---|---|---|---|---|---|---|---|---|---|
| | 1 | 2 | 3 | 4 | 5 | 6 | 7 | 8 | 9 | 10 | 11 |
| BW (%) | 0.62 | −0.80 | −.61 | .40 | −1.49 | 0.57 | 1.20 | −1.47 | −.29 | 0.42 | 1.45 |

To summarize, if we denote the BW values by $y_i$, i=1, 2, . . . n then the autoscaled BW values may be denoted by $$\hat{y}_i = \frac{y_i - \bar{y}}{\sigma} \quad (2)$$

where $$\bar{y} = \frac{\sum_{i=1}^{n} y_i}{n} \quad (3)$$

and $$\sigma = \left[ \frac{\sum_{i=1}^{n}(y_i - \overline{y})^2}{n-1} \right]^{1/2}. \quad (4)$$

The independent variable for the regression is the vector $$\vec{y} = (\hat{y}_1, \hat{y}_2, \ldots \hat{y}_n) \quad (5)$$

The data matrix may be denoted by $$X = (\vec{x}_1, \vec{x}_2, \ldots \vec{x}_N) \quad (6)$$

where $$\vec{x}_i = (x_{i1}, x_{i2}, \ldots x_{iM}) \quad (7)$$

are the individual echo trains M time samples long. The individual echo trains are autoscaled in the same fashion as the y vector. This then gives an autoscaled data matrix $$\hat{X} = [\hat{x}_{ij}], i=1, 2, \ldots M; j=1, 2 \ldots N.$$

By the regression analysis, we come up with a simple relation that gives a predicted value for the autoscaled BW as $$\hat{y}_{pred,i} = \sum_{k=1}^{M} a_k \hat{x}_{ik} + b_i. \quad (8)$$

Figure 8:
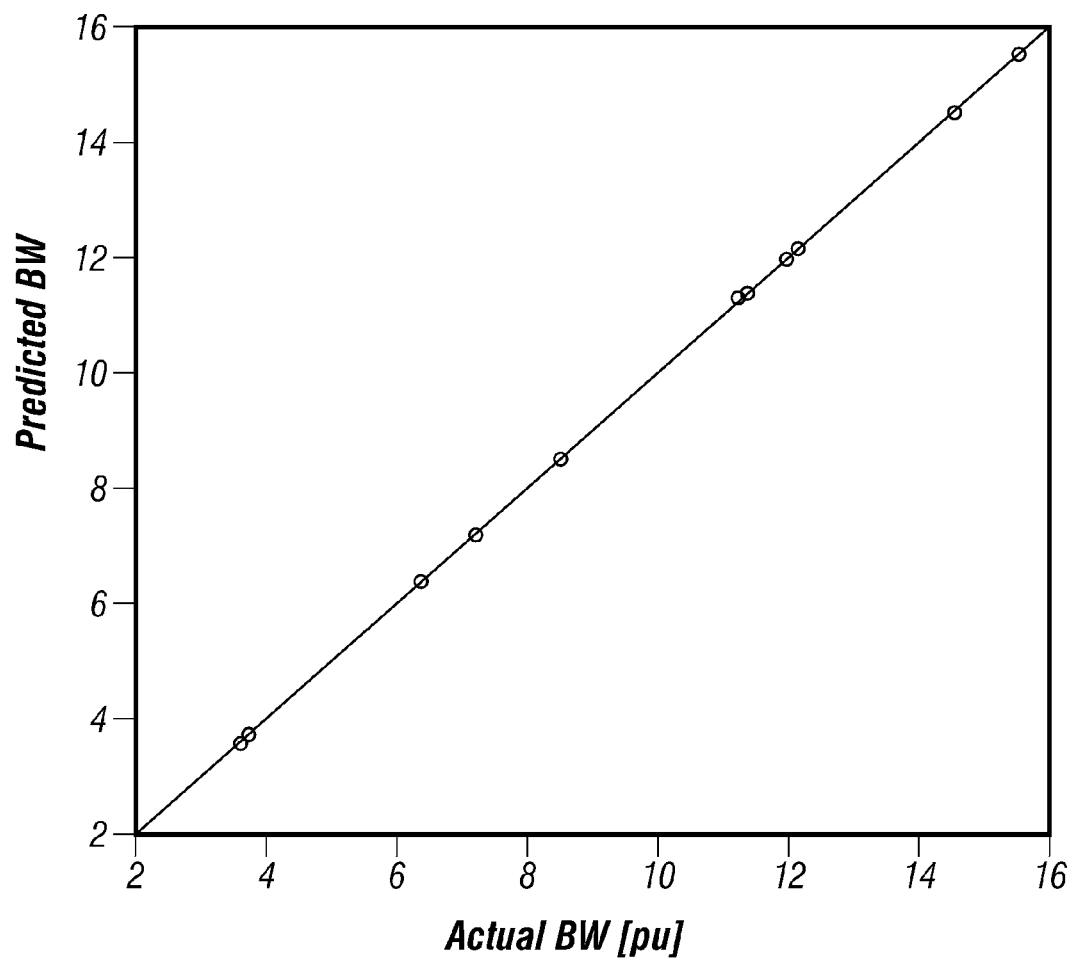
FIG. 8 shows a comparison between actual BW and the predicted BW according to the method of the present disclosure for the training set.

From this, we can recover the unscaled predicted BW. A plot of the unscaled BW against the actual BW appears in FIG. 8. The abscissa is the actual value of BW and the ordinate is the predicted value. Agreement is good and the standard error of the fit is $1.297 \times 10^{-6}$ (obtained from numerical analysis, not apparent from the plot).

The regression model was then validated by applying it to spin echo signals from samples from the Shell Rock Catalog that were not part of the original regression signals. The signals from these additional samples may be called validation signals, i.e., signals obtained from a validation data set used for validating the regression model. The results are summarized in Table III

TABLE III

Comparison of prediction from model with actual BW of validation samples from the Shell Rock Catalog

| Sample Name | Predicted BW | Actual BW |
|---|---|---|
| T2RCS10 | 3.0004 | 3.0 |
| T2RCS19 | 5.9930 | 6.0 |
| T2RCS58 | 10.8772 | 10.9 |
| T2RCS61 | 4.4256 | 4.4 |

As can be seen, the agreement between the predicted values using the PLS and the actual values of BW is excellent.

Figure 9:
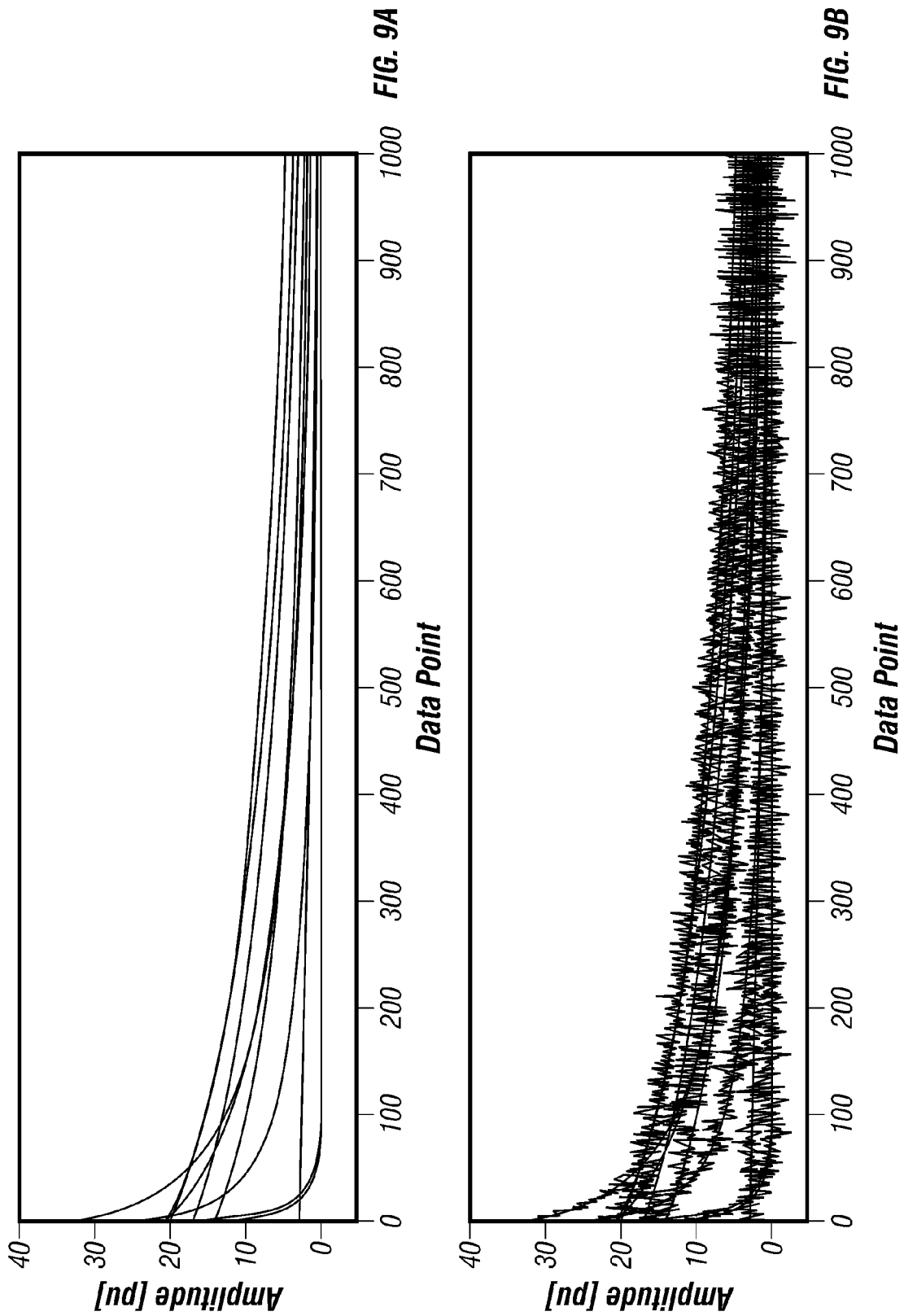
FIGS. 9A and 9B show synthetic NMR spin echo signals without and with additive white noise.
Figure 10:
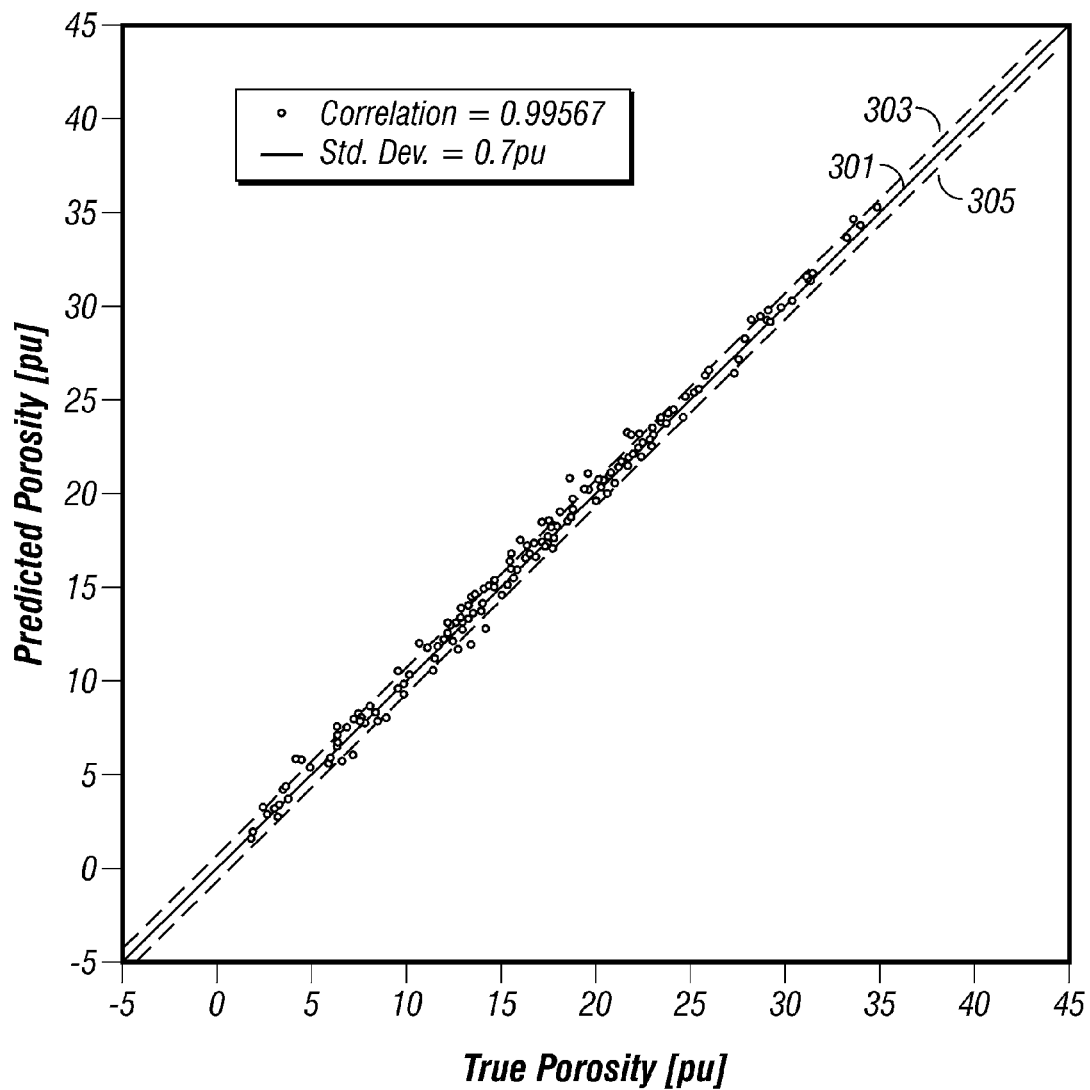
FIG. 10 is a plot of the predicted PHE using the method of the present disclosure against the actual value of PHE for the synthetic NMR signals.

Another example demonstrates the use of the method of the present disclosure for determination of effective porosity from NMR signals. In this example, the training and validation (derivation of prediction relations) is done on synthetic samples (215, 217 in FIG. 3). The top portion of FIG. 9 shows an example of ten synthetic echo trains while the bottom portion of FIG. 9 shows the ten synthetic echo trains with added white noise. FIG. 10 shows the predicted effective porosity (ordinate) plotted against the true effective porosity (abscissa). A total of 200 samples are shown. The regression line 301 and the one standard deviation lines 303, 305 are shown. The standard deviation is 0.7 pu.

Figure 11:
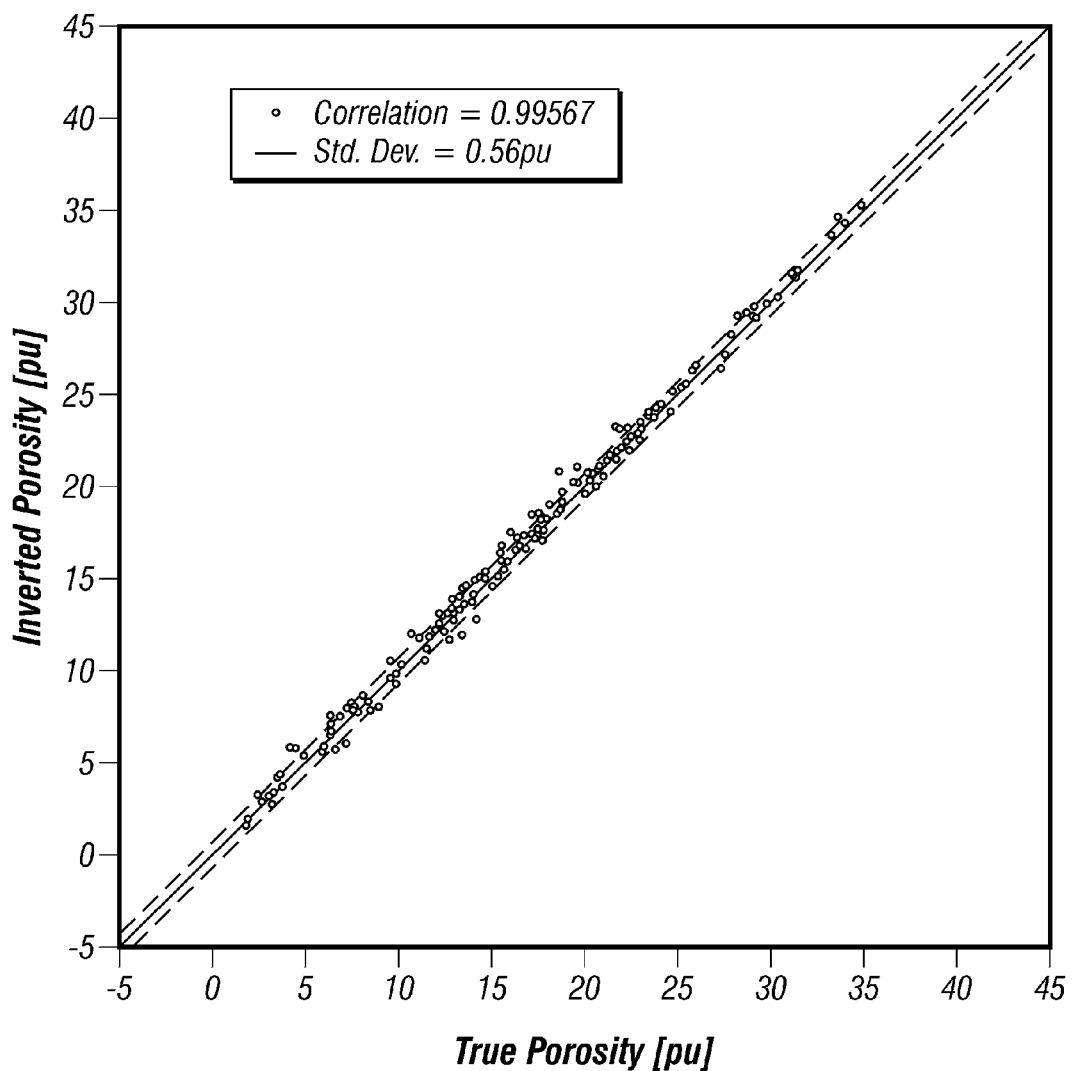
FIG. 11 is a plot of the inverted PHE using a prior art method against the actual value of PHE for the synthetic NMR signals.

To compare the results of the PLS method with prior art methods, the same data were taken and conventional processing was done. The conventional processing comprised an inversion of the echo trains to get a $T_2$ distribution, and determining from the $T_2$ distribution the effective porosity. We refer to this as the "inverted PHE" results. Shown in FIG. 11 is a plot of the inverted PHE (ordinate) against the true porosity (abscissa). The standard deviation of 0.56 pu is slightly less than the results obtained with the PLS.

Figure 12:
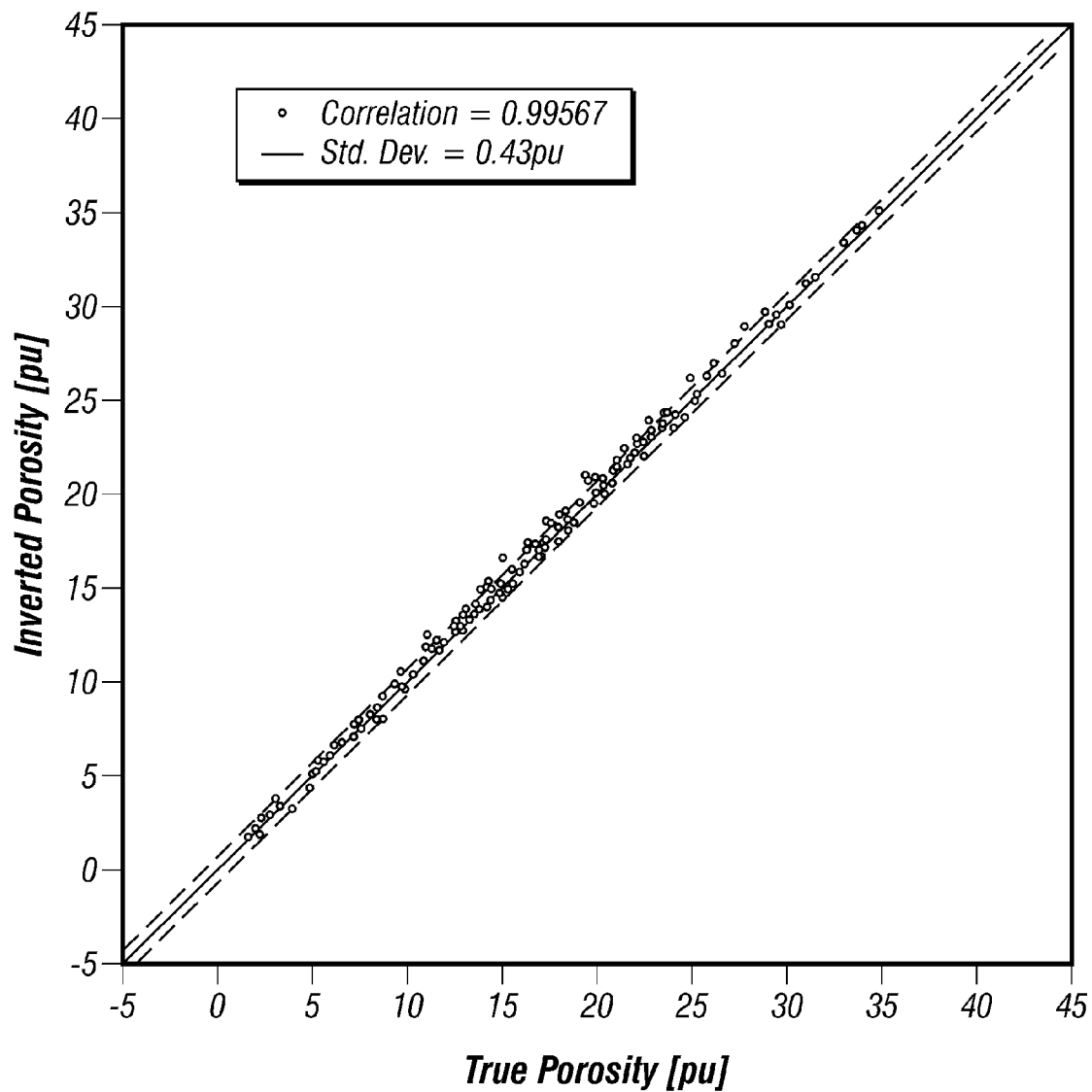
FIG. 12 is a plot of the inverted PHE using a prior art method against the predicted PHE from the method of the present disclosure for the synthetic NMR signals.

FIG. 12 is a plot of the inverted PHE against the predicted porosity from PLS. The standard deviation is smaller than for FIG. 11. This is an indication that the additive noise on the synthetic echo trains (FIG. 9) affected both the PLS method and the inverted PHE results in a similar manner.

Figure 13A:
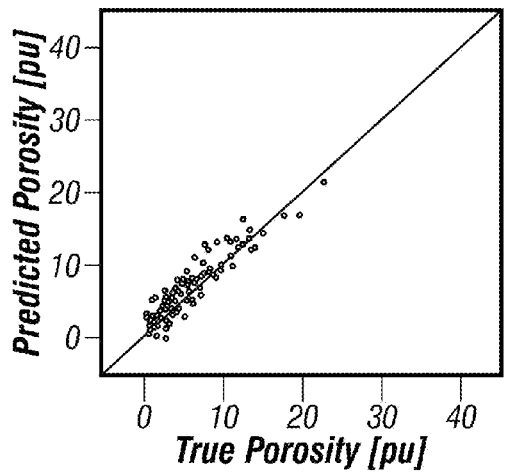
FIGS. 13A-13F shows plots of predicted and actual values of other parameters of interest.
Figure 13B:
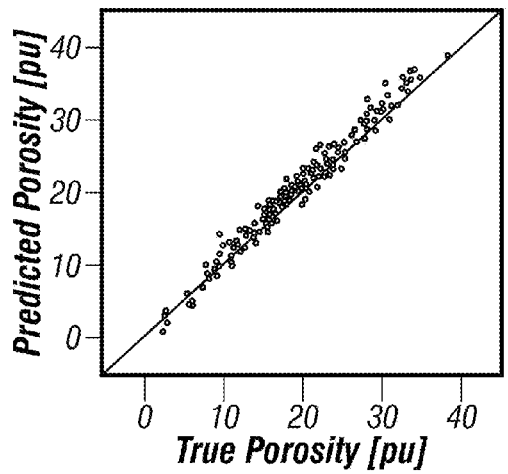
Figure 13C:
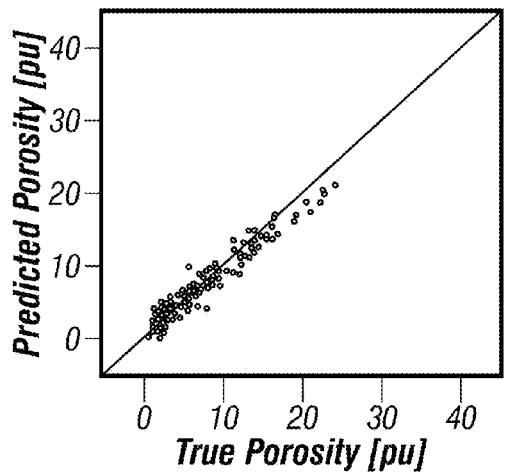
Figure 13D:
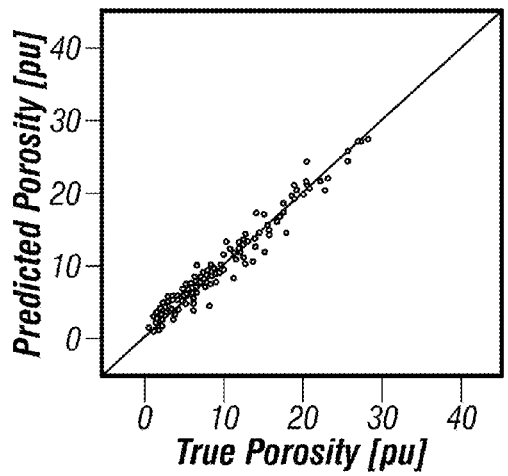
Figure 13E:
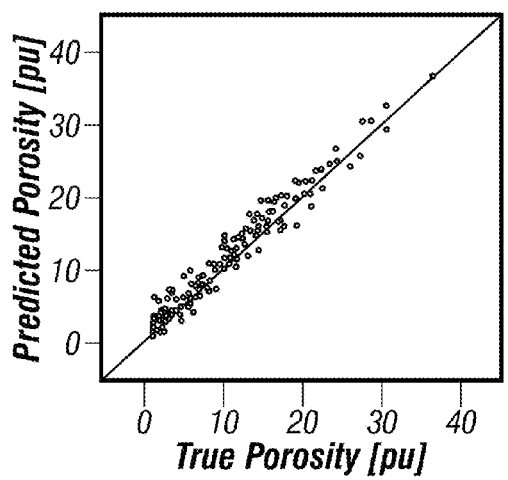
Figure 13F:
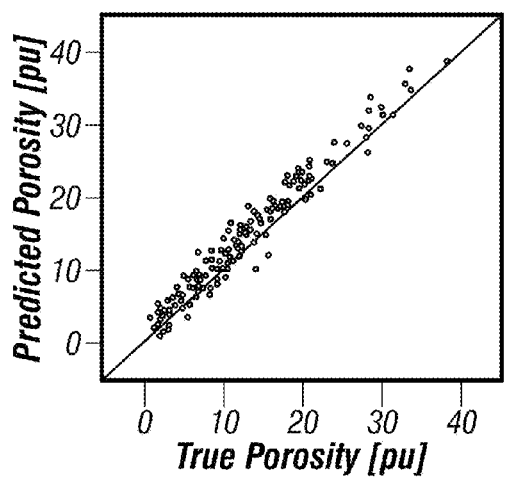

FIGS. 13A-13F shows exemplary plots of other parameters of interest that can be obtained from NMR signals using the method of the present disclosure. Shown in FIG. 13A is a plot of predicted CBW against actual CBW; shown in FIG. 13B is a plot of predicted total porosity against actual total porosity; FIG. 13C is a plot for BVI with a cutoff time appropriate for sandstones; FIG. 13D is a plot of BVI with a cutoff time appropriate for carbonates; FIG. 13E is a plot of BW with a sandstone cutoff; and FIG. 13F is a plot of BW with a carbonate cutoff.

Having demonstrated the applicability of the PLS analysis method for prediction of BW, PHE, BVI, CBW, and BW on rock samples, it is straightforward to apply the results of the regression to in situ measurements made with a MWD or wireline NMR logging device. For the purposes of this disclosure, these measured signals from samples having unknown characteristics may be called evaluation signals (to distinguish them from the training signals used for derivation of the regression and the validation signals used for validating the regression). A specific example of a MWD device has been described, but any suitable device could be used. The method is equally applicable to wireline conveyed NMR instruments. The method directly determines parameters of interest of the earth formation such as the BW, PHE, BVI, CBW, and BW from the NMR signals. By "direct determination" is meant that given a NMR signal, the parameter of interest is obtained by direct application of a simple mathematical operator to the signal. Eqn. (8) is an example of a linear mathematical operator.

In the examples given, a linear regression was adequate to relate a parameter of the earth formation to NMR spin echo signals. When a linear regression is not adequate, it is possible to use nonlinear regression methods to improve the fit to the data. The method is equally applicable to nonlinear regression. As would be known to those versed in the art, increasing the number of dependent variables (e.g., by adding nonlinear terms) will give a better fit, but the fit will have reduced statistical significance. The PLS package provides various measures of the goodness of fit and those versed in statistical analysis would be familiar with tests, such as the F ratio test, to assess the quality of the fit (prediction model). The F test is a well known test based on the number of independent variables and the number of dependent variables, and is not discussed here. The examples presented have involved sandstone samples. The method is equally applicable to other types of rocks, such as carbonate rocks.

In an alternate embodiment of the disclosure, it is not necessary to obtain actual rock samples for doing the training and the validation. For example, in a reservoir development, measurements may be made using a NMR logging tool in a first borehole and a detailed analysis of NMR signals is carried out using prior art methods that require intensive computations. The results of this analysis are applied for both the training set, validation set and the test set using regression method described above. The results of the regression method can then be used in subsequent boreholes drilled in the same geographic area to give real time estimates of the formation properties: application of the results of the predictive model of the present disclosure is quite straightforward and does not require much computing power. Alternatively, the training and validation may be done in a first portion of the borehole and the results applied in a second portion of the borehole. For MWD applications, the first portion could be the shallow portion of the borehole, so that at deeper depths, estimation of the formation properties can be done speedily.

Figure 14:
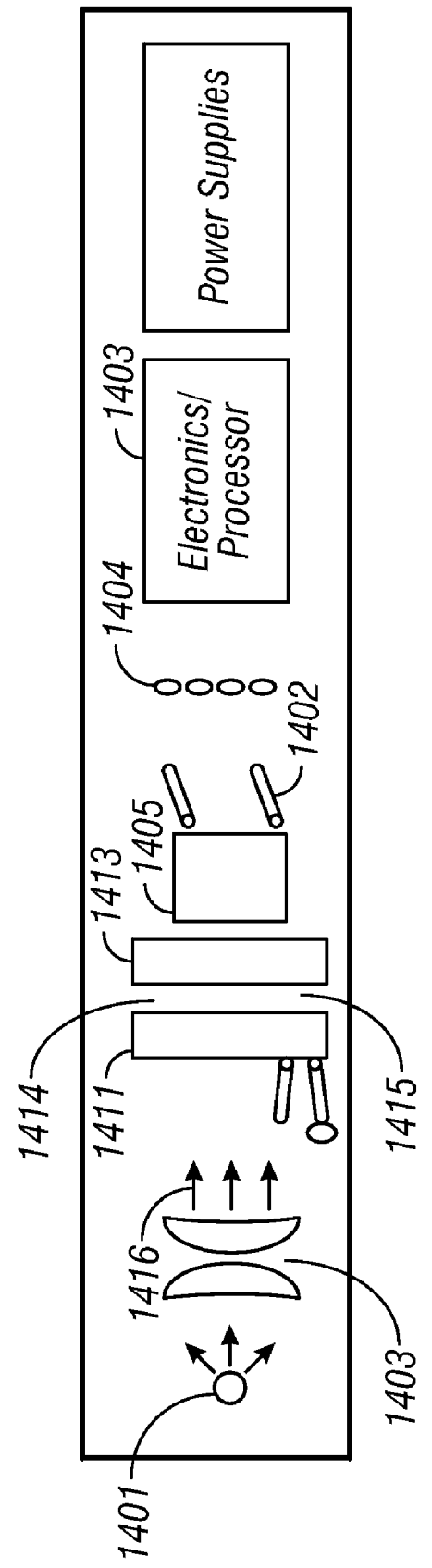
FIG. 14 is a diagram of the Fluid Characterization Module SampleView®.

The methods described above have applicability in other types of measurements made downhole, such as fluid analysis. FIG. 14 illustrates the existing space layout within a downhole fluid characterization module, as, for example, the Baker Atlas SampleView® tool. A light source 1401 (e.g. tungsten light bulb) emits light toward a sample, and a collimating lens device 1403 is positioned between the light source 1401 and the sample collimates this light. The collimated light 1416 is incident generally perpendicular to a first sapphire window 1411. Sapphire windows 1411 and 1403 lie generally perpendicular to the collimated beam of light 1406 and are separated by a gap or channel 1414 enabling a fluid sample 1415 to flow between them. Reflected and fluoresced light can be used to determine sample properties. The existing downhole tools are fitted with a UV light source (e.g. UV LED's), which can be turned on when the tungsten light source 1401 is turned off. A downhole spectrometer 1404 with a detector enables collecting the crude oil fluorescence. In one or more embodiments, the detector may include a semiconductor diode, a photodiode, phototransistor, photoresistor, charge-coupled device, a complimentary metal oxide semiconductor ("CMOS") or any combination thereof. Electronics/processor 1403 acquires and processes the output of the detector. In an exemplary embodiment, the spectrometer is configured to measure spectra between 300 nm and 900 nm, though this is not to be constructed as a limitation.

The fluorescence of a sample fluid recovered downhole depends upon the type of fluid. A strong fluorescence signal is emitted by polycyclic aromatic carbons like anthracene. Lighter crude oils, because of a different chemical composition and shorter chain length of the molecules, fluoresce more intensely in the lower wavelengths region than heavier crudes. The peak of the fluorescence signal moves to longer wavelengths as the crude oil becomes heavier. Due to the phenomenon of self extinction, the signal intensity of heavy and dark crude oils is less. Condensates exhibit fluorescence when they contain poly cyclic compounds. Like light crude oils, condensates fluoresce intensely on the lower wavelengths.

Figure 15:
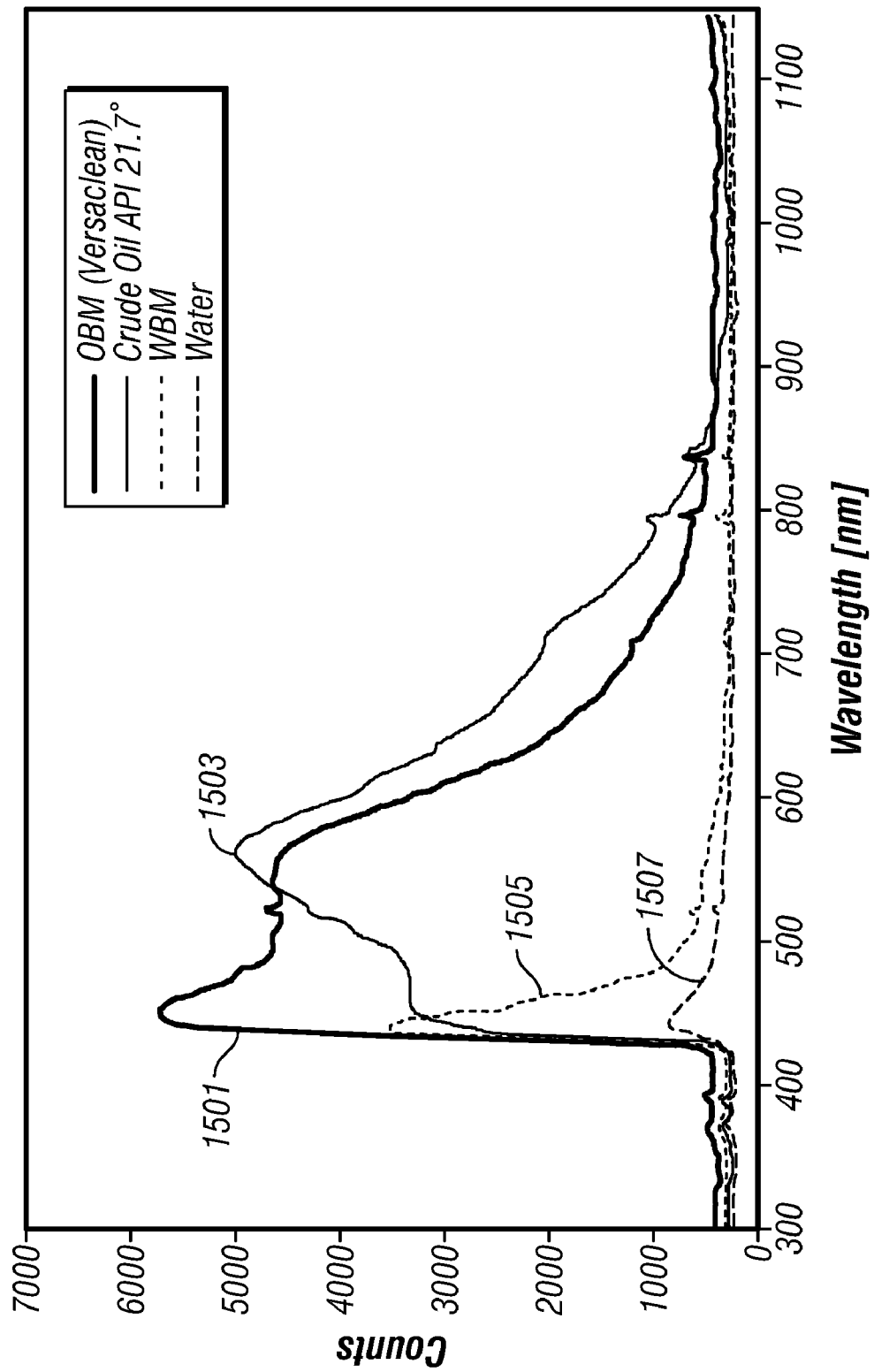
FIG. 15 is a plot showing exemplary fluorescence spectra for oil-based mud (OBM), an exemplary crude oil, water-based mud (WBM) and water.

Fluorescence from dry gas, water and other chemical substances downhole is not significant. Reflection of the UV light from particles, e.g. in water based mud occurs. Depending on the cut-off wavelength of the long pass filter this signal could be eliminated. The fluorescence of oil based mud varies depending on the composition. Main components are different oil based fluids (e.g. esters, olefins or paraffins), water, solids and additives (e.g. fluid loss agents or wetting agents). As oil based fluids typically include short-chain hydrocarbons, fluorescence is in the lower wavelengths region. Fluorescence at other wavelengths is also possible due to additives in the fluid. FIG. 15 shows exemplary fluorescence spectra for OBM 1501, an exemplary crude oil of 21.7 API gravity 1503, WBM 1505 and water 1507.

Figure 16:
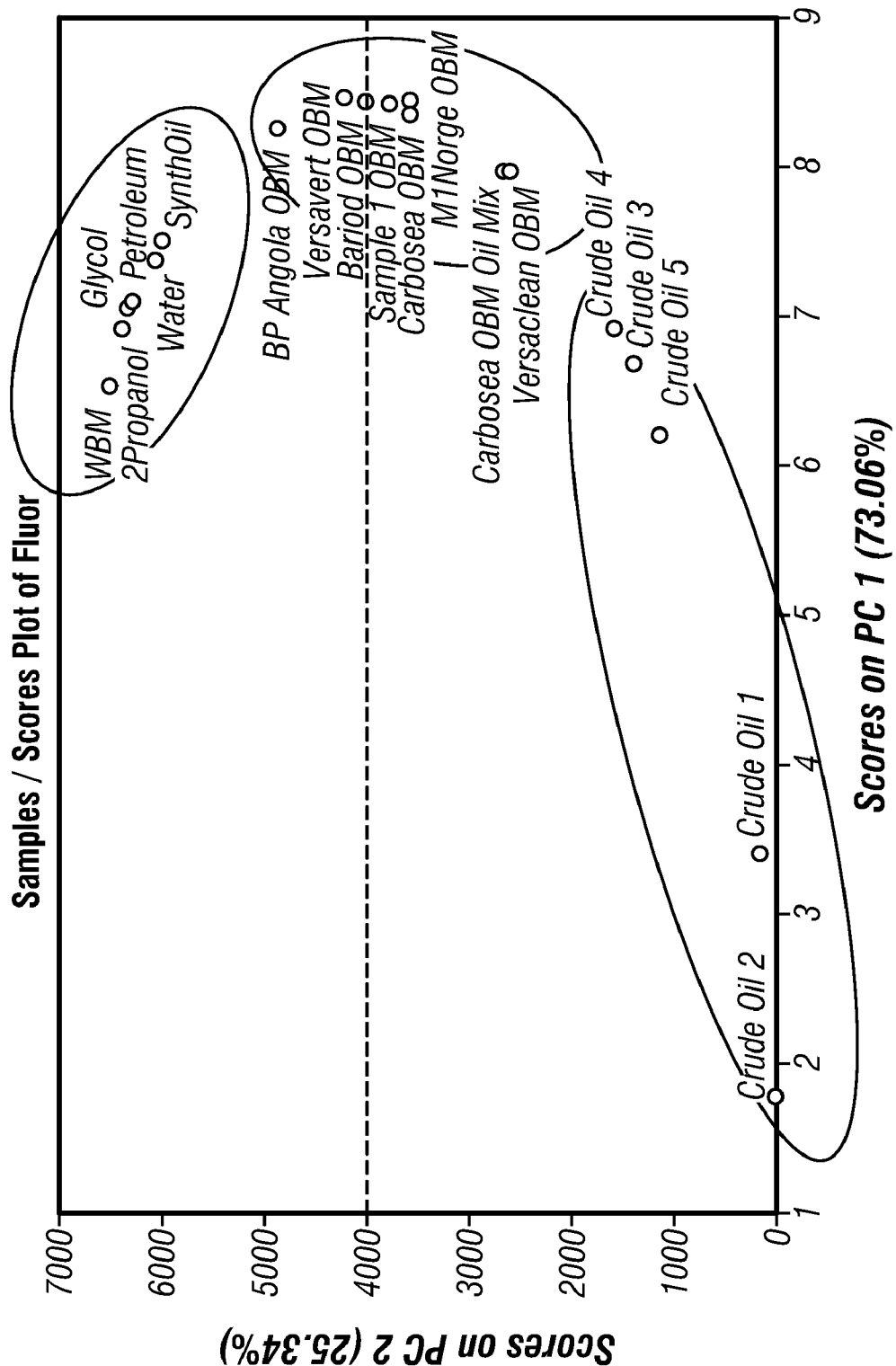
FIG. 16 shows a plot of exemplary fluorescence spectra as a function of the two principal components of the measured spectra of FIG. 15.

Measurements of the spectra for 5 crude oil samples, 8 samples of OBM, water, WBM and additives Glycol, 2-propanol and synthoil have been made. A PCA of the autoscaled fluorescence spectra was carried out and FIG. 16 shows the individual sample points plotted as a function of the two principal components (eigenvectors corresponding to the two principal eigenvalues of the correlation matrix). The spectra fall into three distinct clusters. The cluster indicated by 501 contains crude oil samples, the cluster indicated by 503 contains OBM samples while the cluster indicated by 505 contains water and other fluids.

In one embodiment of the disclosure, a prior art clustering method is used to differentiate the three classes of fluids. It is clear from FIG. 16 that for the example shown, a cluster analysis in the two principal components can separate the classes of interest. This is not to be construed as a limitation, and a clustering program that operates in more than two dimensions may be used. Examples of clustering programs that may be used include those of Statpac, Mixmod, Clustan and KMR. In order to take this approach, two steps are involved. First is the determination of the principal components of a training set, and second is the application of the cluster analysis program in two or more principal components to determine cluster boundaries. Subsequent data samples are projected onto the two or more principal components, and application of the cluster analysis program to identify the particular cluster that the new data sample falls into.

In one embodiment of the disclosure, an Expert System implemented as a Neutral network (NN) is used to perform the clustering. As would be known to those versed in the art, there are three main steps involved in using a NN. The first step is the training of the NN. Required for this is a wide sampling of fluids that are to be analyzed and the corresponding "ground truth", the type of fluid. The second step is the validation of the NN; in the validation process, samples that are different from those used in the training process are input to the NN and the decision of the NN is again compared with the ground truth. If there is agreement, then the NN has been validated. Once the NN has been validated, its structure and parameters may be stored in the processor and NN may then be used to process, preferably in real time, measurements made by the logging device. In a preferred embodiment of the invention, the Stuttgart Neural Net Simulator is used for the training of the NN. It is well within the capabilities of a NN to distinguish between the three classes discussed above, and, in particular, oil based mud filtrate, crude oil and other liquids (like water, water based mud and other oil).

Another embodiment of the disclosure uses the regression methods discussed above to predict the composition of a two component mixture. Instead of the porosity prediction made with NMR measurements, the relative fractions of two components of a fluid mixture can be predicted. For example, the ratio between OBM and oil, and the ratio of crude oil to water may be predicted. The latter prediction is particularly useful in formation testing as it provides an estimate of the saturation of a reservoir, a key factor in estimation of reserves and development of the reservoir.

Those skilled in the art and having benefit of the present disclosure would recognize that the mixtures of three or more fluids can also be analyzed with a modification of the methodology discussed above. Specifically, instead of eqn (8), for a three component fluid mixture, the linear prediction model takes the form:

$$\left[\begin{array}{c}\hat{y}_1\\\hat{y}_2\end{array}\right]_{pred,i}=\sum_{k=1}^{M}\left[\begin{array}{c}a_{1,k}\\a_{2,k}\end{array}\right]\hat{x}_{ik}+\left[\begin{array}{c}b_{1,i}\\b_{2,i}\end{array}\right], \quad (9)$$

where the y-s are relative fractions of two of the three fluid components. The sum of the fluid fractions for three components must be equal to 1.0. For a multicomponent mixture, more parameters have to be estimated and hence a larger training set is needed.

Some of the processing of the data may be done by a downhole processor to give estimates of formation parameters substantially in real time. These can then be telemetered to the surface. Alternatively, the measurements could be recorded downhole, retrieved when the drillstring is tripped, and processed using a surface processor. Implicit in the control and processing of the data is the use of a computer program on a suitable machine readable medium that enables the processor to perform the control and processing. The machine readable medium may include ROMs, EPROMs, EEPROMs, Flash Memories and Optical disks.

While the foregoing disclosure is directed to the specific embodiments of the disclosure, various modifications will be apparent to those skilled in the art. It is intended that all variations within the scope of the appended claims be embraced by the foregoing disclosure.

The invention claimed is:

1. A method of estimating a value of a property of a fluid recovered from an earth formation, the method comprising:
conveying a sensing apparatus into a borehole in the earth formation;
using the sensing apparatus for making a plurality of measurements indicative of the property of the fluid recovered from the earth formation, wherein the measurements comprise fluorescence spectra; and
using a predictive model to estimate from the measured plurality of measurements the value of the property
wherein the property further comprises a fraction of a crude oil, an oil-based mud, a water-based mud, water, or a combination thereof.

2. The method of claim 1 further conveying the sensing apparatus on one of:
(i) a wireline, and (ii) a bottomhole assembly on a drilling tubular.

3. The method of claim 1 wherein the predictive model is obtained by analysis of a projection of the measurements on a plurality of principal components of measurements indicative of the property obtained from a plurality of fluid samples having a known value of the property.

4. The method of claim 3 further conveying the sensing apparatus on one of (i) a wireline, and (ii) a bottomhole assembly on a drilling tubular.

5. The method of claim 3 wherein the analysis further comprises at least one of: (i) using a cluster analysis program, and (ii) using a neural network.

6. An apparatus configured to estimate a value of a property of a fluid recovered from an earth formation, the apparatus comprising:
a sensing apparatus configured to be conveyed into a borehole and make a plurality of measurements indicative of the property of the fluid recovered from the earth formation, wherein the measurements comprise fluorescence spectra; and
a processor configured to:
use a predictive model to estimate from the measured plurality of measurements the value of the property;
wherein the property further comprises a fraction of a crude oil, an oil-based mud, a water-based mud, water, or a combination thereof.

7. The apparatus of claim 6 wherein the sensing apparatus further comprises at least one detector selected from the group consisting of: (i) a semiconductor diode, (ii) a photodiode, (iii) phototransistor, (iv) photoresistor, (v) a charge-coupled device, and (vi) a complimentary metal oxide semiconductor.

8. The apparatus of claim 6 further comprising a conveyance device configured to convey the sensing apparatus on one of (i) a wireline, and (ii) a bottomhole assembly on a drilling tubular.

9. The apparatus of claim 6 wherein the predictive model is obtained by analysis of a projection of the measurements on a plurality of principal components of measurements indicative of the property obtained from a plurality of fluid samples having a known value of the property.

10. The apparatus of claim 9 wherein the sensing apparatus further comprises At least one detector selected from the group consisting of: (i) a semiconductor diode, (ii) a photodiode, (iii) phototransistor, (iv) photoresistor, (v) a charge-coupled device, and (vi) a complimentary metal oxide semiconductor.

11. The apparatus of claim 9 further comprising a conveyance device configured to convey the sensing apparatus, the conveyance device selected from: (i) a wireline, and (ii) a bottomhole assembly on a drilling tubular.

12. The apparatus of claim 9 wherein the analysis the processor is configured to perform further comprises using at least one of: (i) a cluster analysis program, and (ii) a neural network.

13. The method of claim 6 wherein the predictive model used by the processor is obtained by a regression in which the dependent variable of the regression comprises a matrix of values of the measurements indicated of the property of claims from a plurality of fluid samples having a known value of the property, and in which the independent variable of the regression comprises the known value of the property.

14. The apparatus of claim 13 wherein the processor is further configured to perform a regression selected from: (i) a partial least squares regression, and (ii) a linear regression.

15. A non-transitory computer-readable medium having instructions thereon that when read by at least one processor cause the at least one processor to execute a method, the method comprising:
estimating a value of a property of a fluid recovered from an earth formation using measurements made by a sensing apparatus on the fluid and a predictive model wherein the property further comprises a fraction of a crude oil, an oil-based mud, a water-based mud, water, or a combination thereof, and wherein the measurements comprise fluorescence spectra.

16. The computer-readable medium of claim 15 further comprising at least one of: (i) a ROM, (ii) an EPROM, (iii) an EEPROM, (iv) a flash memory, or (v) an optical disk.

17. A non-transitory computer-readable medium having instructions there on that when read by at least one processor cause the at least one processor to execute a method, the method comprising:
estimating a value of a property of a fluid recovered from an earth formation using measurements made by a sensing apparatus on the fluid and a predictive model obtained by analysis of a projection of the measurements on a plurality of principal components of measurements indicative of the property obtained from a plurality of fluid samples having a known value of the property, wherein the measurements comprise fluorescence spectra.

18. The computer-readable medium of claim 17 further comprising at least one of: (i) a ROM, (ii) an EPROM, (iii) an EEPROM, (iv) a flash memory, or (v) an optical disk.

19. The method of claim 1 wherein the predictive model is obtained by a regression in which the dependent variable of the regression comprises a matrix of values of the measurements indicated of the property of claims from a plurality of fluid samples having a known value of the property, and in which the independent variable of the regression comprises the known value of the property.

20. The method of claim 19 wherein the regression comprises one of (i) a partial least squares regression, and (ii) a linear regression.

* * * * *